United States Patent [19]
Desmarais et al.

[11] Patent Number: 6,066,715
[45] Date of Patent: *May 23, 2000

[54] LIGANDS FOR PHOSPHATASE BINDING ASSAY

[75] Inventors: Sylvie Desmarais, Laval; Richard Friesen, Dollard des Ormeaux; Robert Zamboni, Pointe Claire, all of Canada

[73] Assignee: Merck Frosst Canada & Co., Kirkland, Canada

[*] Notice: This patent is subject to a terminal disclaimer.

[21] Appl. No.: 08/964,308

[22] Filed: Nov. 4, 1997

Related U.S. Application Data

[60] Provisional application No. 60/030,411, Nov. 4, 1996.

[51] Int. Cl.$^7$ ............................ A61K 38/00; A61K 38/06
[52] U.S. Cl. ............................................. 530/331; 435/483
[58] Field of Search ............................ 530/331; 435/183

[56] References Cited

U.S. PATENT DOCUMENTS 5,501,969  3/1996  Hastings et al. .................... 435/252.33

OTHER PUBLICATIONS

R. L. Wange et al., "F2(PMP)2–TAM3, A Novel Competitive Inhibitor of the Binding of ZAP–70 to the T Cell Antigen Receptor, Blocks Early T Cell Signaling," J. Biol. Chem., vol. 270, pp. 944–948 (1995).
R. H. Skinner et al., "Direct Measurement of the Binding of RAS to Neurofibtromin Using Scintillation Proximity Assay", Anal. Biochem., vol. 223, pp. 259–265 (1994).
J. A. Patcher et al., "Scintillation Proximity Assay to Measure Binding of Soluble Fibronectin to Antibody–Captured alpha5B1 Integrin", anal. Biochem., vol. 230, pp. 101–107 (1995).
N. A. Tonks et al., "Characterization of the Major Protein–tyrosine–phosphatases of Human Placenta", JBC, pp. 6731–6737 (1988a).
H. Charbonneau et al., "The leukocyte common antigen (CD45): A putative receptor–linked protein tyrosine phosphatase", PNAS 85, pp. 7182–7186, (1988).
N. K. Tonks et al., "Demonstration That the Leukocyte Common Antigen CD45 Is a Protein Tyrosine Phosphatase", Biochemistry 27, pp. 8695–8701 (1988b).
T. Burke et al., "Heterogeneity Of Protein Kinase C Activity IN Human U–373 And G–26 Mice Glioma Cells", Biochem. Biophys. Res Comm., 205, pp. 129–134, (1994).
M. Streuli et al., "A Family of receptor–linked protein tyrosine phosphatases in humans and Drosophila", Proc. Nat'l Acad USA, vol. 86, pp. 8698–7602, Nov. 1989.
J. Chernoff et al., "Cloning of a cDNA for a major human protein–tyrosine phosphatase", Proc. Nat'l Acad Sci. USA, vol. 87, pp/ 2735–2739, Apr. 1990.
D. Bromme et al., "Human Cathepsin O2, a Novel Cysteine Protease Hghly Expressed in Osteoclastomas and Ovary Molecular Cloning, Sequencing and Tissue Distribution-"Biol. Chem. Hoppe–Seyler, vol. 376 pp. 379–384, Jun. 1995.
F. Drake et al., " Cathepsin K, but Not Cathespin B, L, or S, Is Abundantly Expressed in Human Ostheoclasts", J. Biol. Chem. vol. 271, No., 21, pp. 12511–12516 , (1996).
T. Burke et al., "Potent Inhibition of Insulin Receptor Dephorylation By a Hexamer Peptide Containing the Phosphotyrosyl Mimetic F2Pmp", Biochem. Biophys. Res. Comm., vol. 204 pp. 129–134, (1994).
R. Singh & G. M. Whitesides, "A Reagent for Reduction of Disulfide Bonds in Proteins That Reduces Disulfide Bonds Faster Than Does Dithiothreitol", J. Org. Chem. 56, pp. 2323–2337, (1991).

*Primary Examiner*—Michael P. Woodward
*Assistant Examiner*—Michael Borin
*Attorney, Agent, or Firm*—Philippe L. Durette; Melvin Winokur

[57] ABSTRACT

Disclosed are new ligands for use in a binding assay for proteases and phosphatases, which contain cysteine in their binding sites or as a necessary structural component for enzymatic binding. The sulfihydryl group of cysteine is the nucleophilic group in the enzyme's mechanistic proteolytic and hydrolytic properties. The assay can be used to determine the ability of new, unknown ligands and mixtures of compounds to competitively bind with the enzyme versus a known binding agent for the enzyme, e.g., a known enzyme inhibitor. By the use of a mutant form of the natural or native wild-type enzyme, in which serine, or another amino acid, e.g., alanine, replaces cysteine, the problem of interference from extraneous oxidizing and alkylating agents in the assay procedure is overcome. The interference arises because of oxidation or alkylation of the sulfihydryl, —SH (or —S$^-$), in the cysteine, which then adversely affects the binding ability of the enzyme. Specifically disclosed is an assay for tyrosine phosphatases and cysteine proteases, including capsases and cathepsins, e.g., Cathepsin K(O2), utilizing scintillation proximity assay (SPA) technology. The assay has important applications in the discovery of compounds for the treatment and study of, for example, diabetes, immunosuppression, cancer, Alzheimer's disease and osteoporosis. The novel feature of the use of a mutant enzyme can be extended to its use in a wide variety of conventional colorimetric, photometric, spectrophotometric, radioimmunoassay and ligand-binding competitive assays.

4 Claims, 8 Drawing Sheets

```
              ATGGAGATGGAAAAGGAGTTCGAGCAGATCGACAAGTCCGGGAGCTGGGCGGCCATTTAC
     1        ---------+---------+---------+---------+---------+---------+    60
              TACCTCTACCTTTTCCTCAAGCTCGTCTAGCTGTTCAGGCCCTCGACCCGCCGGTAAATG
     1        MetGluMetGluLysGluPheGluGlnIleAspLysSerGlySerTrpAlaAlaIleTyr    20

CAGGATATCCGACATGAAGCCAGTGACTTCCCATGTAGAGTGGCCAAGCTTCCTAAGAAC
    61        ---------+---------+---------+---------+---------+---------+   120
              GTCCTATAGGCTGTACTTCGGTCACTGAAGGGTACATCTCACCGGTTCGAAGGATTCTTG
    21        GlnAspIleArgHisGluAlaSerAspPheProCysArgValAlaLysLeuProLysAsn    40

AAAAACCGAAATAGGTACAGAGACGTCAGTCCCTTTGACCATAGTCGGATTAAACTACAT
   121        ---------+---------+---------+---------+---------+---------+   180
              TTTTTGGCTTTATCCATGTCTCTGCAGTCAGGGAAACTGGTATCAGCCTAATTTGATGTA
    41        LysAsnArgAsnArgTyrArgAspValSerProPheAspHisSerArgIleLysLeuHis    60

CAAGAAGATAATGACTATATCAACGCTAGTTTGATAAAAATGGAAGAAGCCCAAAGGAGT
   181        ---------+---------+---------+---------+---------+---------+   240
              GTTCTTCTATTACTGATATAGTTGCGATCAAACTATTTTTACCTTCTTCGGGTTTCCTCA
    61        GlnGluAspAsnAspTyrIleAsnAlaSerLeuIleLysMetGluGluAlaGlnArgSer    80

TACATTCTTACCCAGGGCCCTTTGCCTAACACATGCGGTCACTTTTGGGAGATGGTGTGG
   241        ---------+---------+---------+---------+---------+---------+   300
              ATGTAAGAATGGGTCCCGGGAAACGGATTGTGTACGCCAGTGAAAACCCTCTACCACACC
    81        TyrIleLeuThrGlnGlyProLeuProAsnThrCysGlyHisPheTrpGluMetValTrp   100

GAGCAGAAAAGCAGGGGTGTCGTCATGCTCAACAGAGTGATGGAGAAAGGTTCGTTAAAA
   301        ---------+---------+---------+---------+---------+---------+   360
              CTCGTCTTTTCGTCCCCACAGCAGTACGAGTTGTCTCACTACCTCTTTCCAAGCAATTTT
   101        GluGlnLysSerArgGlyValValMetLeuAsnArgValMetGluLysGlySerLeuLys   120

TGCGCACAATACTGGCCACAAAAAGAAGAAAAAGAGATGATCTTTGAAGACACAAATTTG
   361        ---------+---------+---------+---------+---------+---------+   420
              ACGCGTGTTATGACCGGTGTTTTTCTTCTTTTTCTCTACTAGAAACTTCTGTGTTTAAAC
   121        CysAlaGlnTyrTrpProGlnLysGluGluLysGluMetIlePheGluAspThrAsnLeu   140

AAATTAACATTGATCTCTGAAGATATCAAGTCATATTATACAGTGCGACAGCTAGAATTG
   421        ---------+---------+---------+---------+---------+---------+   480
              TTTAATTGTAACTAGAGACTTCTATAGTTCAGTATAATATGTCACGCTGTCGATCTTAAC
   141        LysLeuThrLeuIleSerGluAspIleLysSerTyrTyrThrValArgGlnLeuGluLeu   160

GAAAACCTTACAACCCAAGAAACTCGAGAGATCTTACATTTCCACTATACCACATGGCCT
   481        ---------+---------+---------+---------+---------+---------+   540
              CTTTTGGAATGTTGGGTTCTTTGAGCTCTCTAGAATGTAAAGGTGATATGGTGTACCGGA
   161        GluAsnLeuThrThrGlnGluThrArgGluIleLeuHisPheHisTyrThrThrTrpPro   180
```

FIGURE 2A

```
        GACTTTGGAGTCCCTGAATCACCAGCCTCATTCTTGAACTTTCTTTTCAAAGTCCGAGAG
541     ---------+---------+---------+---------+---------+---------+  600
        CTGAAACCTCAGGGACTTAGTGGTCGGAGTAAGAACTTGAAAGAAAAGTTTCAGGCTCTC
181     AspPheGlyValProGluSerProAlaSerPheLeuAsnPheLeuPheLysValArgGlu  200

TCAGGGTCACTCAGCCCGGAGCACGGGCCCGTTGTGGTGCACTGCAGTGCAGGCATCGGC
601     ---------+---------+---------+---------+---------+---------+  660
        AGTCCCAGTGAGTCGGGCCTCGTGCCCGGGCAACACCACGTGACGTCACGTCCGTAGCCG
201     SerGlySerLeuSerProGluHisGlyProValValValHisCysSerAlaGlyIleGly  220

AGGTCTGGAACCTTCTGTCTGGCTGATACCTGCCTCCTGCTGATGGACAAGAGGAAAGAC
661     ---------+---------+---------+---------+---------+---------+  720
        TCCAGACCTTGGAAGACAGACCGACTATGGACGGAGGACGACTACCTGTTCTCCTTTCTG
221     ArgSerGlyThrPheCysLeuAlaAspThrCysLeuLeuLeuMetAspLysArgLysAsp  240

CCTTCTTCCGTTGATATCAAGAAAGTGCTGTTAGAAATGAGGAAGTTTCGGATGGGGTTG
721     ---------+---------+---------+---------+---------+---------+  780
        GGAAGAAGGCAACTATAGTTCTTTCACGACAATCTTTACTCCTTCAAAGCCTACCCCAAC
241     ProSerSerValAspIleLysLysValLeuLeuGluMetArgLysPheArgMetGlyLeu  260

ATCCAGACAGCCGACCAGCTGCGCTTCTCCTACCTGGCTGTGATCGAAGGTGCCAAATTC
781     ---------+---------+---------+---------+---------+---------+  840
        TAGGTCTGTCGGCTGGTCGACGCGAAGAGGATGGACCGACACTAGCTTCCACGGTTTAAG
261     IleGlnThrAlaAspGlnLeuArgPheSerTyrLeuAlaValIleGluGlyAlaLysPhe  280

ATCATGGGGGACTCTTCCGTGCAGGATCAGTGGAAGGAGCTTTCCCACGAGGACCTGGAG
841     ---------+---------+---------+---------+---------+---------+  900
        TAGTACCCCCTGAGAAGGCACGTCCTAGTCACCTTCCTCGAAAGGGTGCTCCTGGACCTC
281     IleMetGlyAspSerSerValGlnAspGlnTrpLysGluLeuSerHisGluAspLeuGlu  300

CCCCCACCCGAGCATATCCCCCCACCTCCCCGGCCACCCAAACGAATCCTGGAGCCACACTGA
901     ---------+---------+---------+---------+---------+---------+--- 960
        GGGGGTGGGCTCGTATAGGGGGGTGGAGGGGCCGGTGGGTTTGCTTAGGACCTCGGTGTGACT
301     ProProProGluHisIleProProProProArgProProLysArgIleLeuGluProHisEnd 320
```

FIGURE 2B

```
            GAAACAAGCACTGGATTCCATATCCCACTGCCAAAACCGCATGGTTCAGATTATCGCTAT
      1     ---------+---------+---------+---------+---------+---------+     60
            CTTTGTTCGTGACCTAAGGTATAGGGTGACGGTTTTGGCGTACCAAGTCTAATAGCGATA

TGCAGCTTTCATCATAATACACACCTTTGCTGCCGAAACGAAGCCAGACAACAGATTTCC
      61    ---------+---------+---------+---------+---------+---------+     120
            ACGTCGAAAGTAGTATTATGTGTGGAAACGACGGCTTTGCTTCGGTCTGTTGTCTAAAGG

ATCAGCAGGATGTGGGGGCTCAAGGTTCTGCTGCTACCTGTGGTGAGCTTTGCTCTGTAC
      121   ---------+---------+---------+---------+---------+---------+     180
            TAGTCGTCCTACACCCCCGAGTTCCAAGACGACGATGGACACCACTCGAAACGAGACATG
                       MetTrpGlyLeuLysValLeuLeuLeuProValSerPheAlaLeuTyr

CCTGAGGAGATACTGGACACCCACTGGGAGCTATGGAAGAAGACCCACAGGAAGCAATAT
      181   ---------+---------+---------+---------+---------+---------+     240
            GGACTCCTCTATGACCTGTGGGTGACCCTCGATACCTTCTTCTGGGTGTCCTTCGTTATA
            ProGluGluIleLeuAspThrHisTrpGluLeuTrpLysLysThrHisArgLysGlnTyr

AACAACAAGGTGGATGAAATCTCTCGGCGTTTAATTTGGGAAAAAAACCTGAAGTATATT
      241   ---------+---------+---------+---------+---------+---------+     300
            TTGTTGTTCCACCTACTTTAGAGAGCCGCAAATTAAACCCTTTTTTTGGACTTCATATAA
            AsnAsnLysValAspGluIleSerArgArgLeuIleTrpGluLysAsnLeuLysTyrIle

TCCATCCATAACCTTGAGGCTTCTCTTGGTGTCCATACATATGAACTGGCTATGAACCAC
      301   ---------+---------+---------+---------+---------+---------+     360
            AGGTAGGTATTGGAACTCCGAAGAGAACCACAGGTATGTATACTTGACCGATACTTGGTG
            SerIleHisAsnLeuGluAlaSerLeuGlyValHisThrTyrGluLeuAlaMetAsnHis

CTGGGGGACATGACCAGTGAAGAGGTGGTTCAGAAGATGACTGGACTCAAAGTACCCCTG
      361   ---------+---------+---------+---------+---------+---------+     420
            GACCCCCTGTACTGGTCACTTCTCCACCAAGTCTTCTACTGACCTGAGTTTCATGGGGAC
            LeuGlyAspMetThrSerGluGluValValGlnLysMetThrGlyLeuLysValProLeu

TCTCATTCCCGCAGTAATGACACCCTTTATATCCCAGAATGGGAAGGTAGAGCCCCAGAC
      421   ---------+---------+---------+---------+---------+---------+     480
            AGAGTAAGGGCGTCATTACTGTGGGAAATATAGGGTCTTACCCTTCCATCTCGGGGTCTG
            SerHisSerArgSerAsnAspThrLeuTyrIleProGluTrpGluGlyArgAlaProAsp

TCTGTCGACTATCGAAAGAAAGGATATGTTACTCCTGTCAAAAATCAGGGTCAGTGTGGT
      481   ---------+---------+---------+---------+---------+---------+     540
            AGACAGCTGATAGCTTTCTTTCCTATACAATGAGGACAGTTTTTAGTCCCAGTCACACCA
            SerValAspTyrArgLysLysGlyTyrValThrProValLysAsnGlnGlyGlnCysGly
```

FIGURE 3A

```
            TCCTGTTGGGCTTTTAGCTCTGTGGGTGCCCTGGAGGGCCAACTCAAGAAGAAAACTGGC
     541    ------------+---------+---------+---------+---------+---------+  600
            AGGACAACCCGAAAATCGAGACACCCACGGGACCTCCCGGTTGAGTTCTTCTTTTGACCG
            SerCysTrpAlaPheSerSerValGlyAlaLeuGluGlyGlnLeuLysLysThrGly
                                                                      139

AAACTCTTAAATCTGAGTCCCCAGAACCTAGTGGATTGTGTGTCTGAGAATGATGGCTGT
     601    ---------+---------+---------+---------+---------+---------+  660
            TTTGAGAATTTAGACTCAGGGGTCTTGGATCACCTAACACACAGACTCTTACTACCGACA
            LysLeuLeuAsnLeuSerProGlnAsnLeuValAspCysValSerGluAsnAspGlyCys

GGAGGGGGCTACATGACCAATGCCTTCCAATATGTGCAGAAGAACCGGGGTATTGACTCT
     661    ---------+---------+---------+---------+---------+---------+  720
            CCTCCCCCGATGTACTGGTTACGGAAGGTTATACACGTCTTCTTGGCCCCATAACTGAGA
            GlyGlyGlyTyrMetThrAsnAlaPheGlnTyrValGlnLysAsnArgGlyIleAspSer

GAAGATGCCTACCCATATGTGGGACAGGAAGAGAGTTGTATGTACAACCCAACAGGCAAG
     721    ---------+---------+---------+---------+---------+---------+  780
            CTTCTACGGATGGGTATACACCCTGTCCTTCTCTCAACATACATGTTGGGTTGTCCGTTC
            GluAspAlaTyrProTyrValGlyGlnGluGluSerCysMetTyrAsnProThrGlyLys

GCAGCTAAATGCAGAGGGTACAGAGAGATCCCCGAGGGGAATGAGAAAGCCCTGAAGAGG
     781    ---------+---------+---------+---------+---------+---------+  840
            CGTCGATTTACGTCTCCCATGTCTCTCTAGGGGCTCCCCTTACTCTTTCGGGACTTCTCC
            AlaAlaLysCysArgGlyTyrArgGluIleProGluGlyAsnGluLysAlaLeuLysArg

GCAGTGGCCCGAGTGGGACCTGTCTCTGTGGCCATTGATGCAAGCCTGACCTCCTTCCAG
     841    ---------+---------+---------+---------+---------+---------+  900
            CGTCACCGGGCTCACCCTGGACAGAGACACCGGTAACTACGTTCGGACTGGAGGAAGGTC
            AlaValAlaArgValGlyProValSerValAlaIleAspAlaSerLeuThrSerPheGln

TTTTACAGCAAAGGTGTGTATTATGATGAAAGCTGCAATAGCGATAATCTGAACCATGCG
     901    ---------+---------+---------+---------+---------+---------+  960
            AAAATGTCGTTTCCACACATAATACTACTTTCGACGTTATCGCTATTAGACTTGGTACGC
            PheTyrSerLysGlyValTyrTyrAspGluSerCysAsnSerAspAsnLeuAsnHisAla

GTTTTGGCAGTGGGATATGGAATCCAGAAGGGAAACAAGCACTGGATAATTAAAAACAGC
     961    ---------+---------+---------+---------+---------+---------+ 1020
            CAAAACCGTCACCCTATACCTTAGGTCTTCCCTTTGTTCGTGACCTATTAATTTTTGTCG
            ValLeuAlaValGlyTyrGlyIleGlnLysGlyAsnLysHisTrpIleIleLysAsnSer

TGGGGAGAAAACTGGGGAAACAAAGGATATATCCTCATGGCTCGAAATAAGAACAACGCC
    1021    ---------+---------+---------+---------+---------+---------+ 1080
            ACCCCTCTTTTGACCCCTTTGTTTCCTATATAGGAGTACCGAGCTTTATTCTTGTTGCGG
            TrpGlyGluAsnTrpGlyAsnLysGlyTyrIleLeuMetAlaArgAsnLysAsnAsnAla
```

FIGURE 3B

```
        TGTGGCATTGCCAACCTGGCCAGCTTCCCCAAGATGTGACTCCAGCCAGCCAAATCCATC
1081    ---------+---------+---------+---------+---------+---------+    1140
        ACACCGTAACGGTTGGACCGGTCGAAGGGGTTCTACACTGAGGTCGGTCGGTTTAGGTAG
        CysGlyIleAlaAsnLeuAlaSerPheProLysMetEnd

CTGCTCTTCCATTTCTTCCACGATGGTGCAGTGTAACGATGCACTTTGGAAGGGAGTTGG
1141    ---------+---------+---------+---------+---------+---------+    1200
        GACGAGAAGGTAAAGAAGGTGCTACCACGTCACATTGCTACGTGAAACCTTCCCTCAACC

TGTGCTATTTTTGAAGCAGATGTGGTGATACTGAGATTGTCTGTTCAGTTTCCCCATTTG
1201    ---------+---------+---------+---------+---------+---------+    1260
        ACACGATAAAACTTCGTCTACACCACTATGACTCTAACAGACAAGTCAAAGGGGTAAAC

TTTGTGCTTCAAATGATCCTTCCTACTTTGCTTCTCTCCACCCATGACCTTTTTCACTGT
1261    ---------+---------+---------+---------+---------+---------+    1320
        AAACACGAAGTTTACTAGGAAGGATGAAACGAAGAGAGGTGGGTACTGGAAAAAGTGACA

GGCCATCAGGACTTTCCCTGACAGCTGTGTACTCTTAGGCTAAGAGATGTGACTACAGCC
1321    ---------+---------+---------+---------+---------+---------+    1380
        CCGGTAGTCCTGAAAGGGACTGTCGACACATGAGAATCCGATTCTCTACACTGATGTCGG

TGCCCCTGACTGTGTTGTCCCAGGGCTGATGCTGTACAGGTACAGGCTGGAGATTTTCAC
1381    ---------+---------+---------+---------+---------+---------+    1440
        ACGGGGACTGACACAACAGGGTCCCGACTACGACATGTCCATGTCCGACCTCTAAAAGTG

ATAGGTTAGATTCTCATTCACGGGACTAGTTAGCTTTAAGCACCCTAGAGGACTAGGGTA
1441    ---------+---------+---------+---------+---------+---------+    1500
        TATCCAATCTAAGAGTAAGTGCCCTGATCAATCGAAATTCGTGGGATCTCCTGATCCCAT

ATCTGACTTCTCACTTCCTAAGTTCCCTTCTATATCCTCAAGGTAGAAATGTCTATGTTT
1501    ---------+---------+---------+---------+---------+---------+    1560
        TAGACTGAAGAGTGAAGGATTCAAGGGAAGATATAGGAGTTCCATCTTTACAGATACAAA

TCTACTCCAATTCATAAATCTATTCATAAGTCTTTGGTACAAGTTTACATGATAAAAAGA
1561    ---------+---------+---------+---------+---------+---------+    1620
        AGATGAGGTTAAGTATTTAGATAAGTATTCAGAAACCATGTTCAAATGTACTATTTTTCT

AATGTGATTTGTCTTCCCTTCTTTGCACTTTTGAAATAAAGTATTTATC
1621    ---------+---------+---------+---------+---------           1669
        TTACACTAAACAGAAGGGAAGAAACGTGAAAACTTTATTTCATAAATAG
```

FIGURE 3C

```
      CTGCAGGAATTCGGCACGAGGGGTGCTATTGTGAGGCGGTTGTAGAAGTTAATAAAGGTA
   1  ---------+---------+---------+---------+---------+---------+   60
      GACGTCCTTAAGCCGTGCTCCCCACGATAACACTCCGCCAACATCTTCAATTATTTCCAT

TCCATGGAGAACACTGAAAACTCAGTGGATTCAAAATCCATTAAAAATTTGGAACCAAAG
  61  ---------+---------+---------+---------+---------+---------+  120
      AGGTACCTCTTGTGACTTTTGAGTCACCTAAGTTTTAGGTAATTTTTAAACCTTGGTTTC
          MetGluAsnThrGluAsnSerValAspSerLysSerIleLysAsnLeuGluProLys

ATCATACATGGAAGCGAATCAATGGACTCTGGAATATCCCTGGACAACAGTTATAAAATG
 121  ---------+---------+---------+---------+---------+---------+  180
      TAGTATGTACCTTCGCTTAGTTACCTGAGACCTTATAGGGACCTGTTGTCAATATTTTAC
      IleIleHisGlySerGluSerMetAspSerGlyIleSerLeuAspAsnSerTyrLysMet

GATTATCCTGAGATGGGTTTATGTATAATAATTAATAATAAGAATTTTCATAAGAGCACT
 181  ---------+---------+---------+---------+---------+---------+  240
      CTAATAGGACTCTACCCAAATACATATTATTAATTATTATTCTTAAAAGTATTCTCGTGA
      AspTyrProGluMetGlyLeuCysIleIleIleAsnAsnLysAsnPheHisLysSerThr

GGAATGACATCTCGGTCTGGTACAGATGTCGATGCAGCAAACCTCAGGGAAACATTCAGA
 241  ---------+---------+---------+---------+---------+---------+  300
      CCTTACTGTAGAGCCAGACCATGTCTACAGCTACGTCGTTTGGAGTCCCTTTGTAAGTCT
      GlyMetThrSerArgSerGlyThrAspValAspAlaAlaAsnLeuArgGluThrPheArg

AACTTGAAATATGAAGTCAGGAATAAAAATGATCTTACACGTGAAGAAATTGTGGAATTG
 301  ---------+---------+---------+---------+---------+---------+  360
      TTGAACTTTATACTTCAGTCCTTATTTTTACTAGAATGTGCACTTCTTTAACACCTTAAC
      AsnLeuLysTyrGluValArgAsnLysAsnAspLeuThrArgGluGluIleValGluLeu

ATGCGTGATGTTTCTAAAGAAGATCACAGCAAAAGGAGCAGTTTTGTTTGTGTGCTTCTG
 361  ---------+---------+---------+---------+---------+---------+  420
      TACGCACTACAAAGATTTCTTCTAGTGTCGTTTTCCTCGTCAAAACAAACACACGAAGAC
      MetArgAspValSerLysGluAspHisSerLysArgSerSerPheValCysValLeuLeu

AGCCATGGTGAAGAAGGAATAATTTTTGGAACAAATGGACCTGTTGACCTGAAAAAAATA
 421  ---------+---------+---------+---------+---------+---------+  480
      TCGGTACCACTTCTTCCTTATTAAAAACCTTGTTTACCTGGACAACTGGACTTTTTTTAT
      SerHisGlyGluGluGlyIleIlePheGlyThrAsnGlyProValAspLeuLysLysIle

ACAAACTTTTTCAGAGGGGATCGTTGTAGAAGTCTAACTGGAAAACCCAAACTTTTCATT
 481  ---------+---------+---------+---------+---------+---------+  540
      TGTTTGAAAAGTCTCCCCTAGCAACATCTTCAGATTGACCTTTTGGGTTTGAAAAGTAA
      ThrAsnPhePheArgGlyAspArgCysArgSerLeuThrGlyLysProLysLeuPheIle
```

FIGURE 4A

```
      ATTCAGGCCTGCCGTGGTACAGAACTGGACTGTGGCATTGAGACAGACAGTGGTGTTGAT
541   ---------+---------+---------+---------+---------+---------+  600
      TAAGTCCGGACGGCACCATGTCTTGACCTGACACCGTAACTCTGTCTGTCACCACAACTA
      IleGlnAlaCysArgGlyThrGluLeuAspCysGlyIleGluThrAspSerGlyValAsp
                163

GATGACATGGCGTGTCATAAAATACCAGTGGAGGCCGACTTCTTGTATGCATACTCCACA
601   ---------+---------+---------+---------+---------+---------+  660
      CTACTGTACCGCACAGTATTTTATGGTCACCTCCGGCTGAAGAACATACGTATGAGGTGT
      AspAspMetAlaCysHisLysIleProValGluAlaAspPheLeuTyrAlaTyrSerThr

GCACCTGGTTATTATTCTTGGCGAAATTCAAAGGATGGCTCCTGGTTCATCCAGTCGCTT
661   ---------+---------+---------+---------+---------+---------+  720
      CGTGGACCAATAATAAGAACCGCTTTAAGTTTCCTACCGAGGACCAAGTAGGTCAGCGAA
      AlaProGlyTyrTyrSerTrpArgAsnSerLysAspGlySerTrpPheIleGlnSerLeu

TGTGCCATGCTGAAACAGTATGCCGACAAGCTTGAATTTATGCACATTCTTACCCGGGTT
721   ---------+---------+---------+---------+---------+---------+  780
      ACACGGTACGACTTTGTCATACGGCTGTTCGAACTTAAATACGTGTAAGAATGGGCCCAA
      CysAlaMetLeuLysGlnTyrAlaAspLysLeuGluPheMetHisIleLeuThrArgVal

AACCGAAAGGTGGCAACAGAATTTGAGTCCTTTTCCTTTGACGCTACTTTTCATGCAAAG
781   ---------+---------+---------+---------+---------+---------+  840
      TTGGCTTTCCACCGTTGTCTTAAACTCAGGAAAAGGAAACTGCGATGAAAAGTACGTTTC
      AsnArgLysValAlaThrGluPheGluSerPheSerPheAspAlaThrPheHisAlaLys

AAACAGATTCCATGTATTGTTTCCATGCTCACAAAAGAACTCTATTTTTATCACTAAAGA
841   ---------+---------+---------+---------+---------+---------+  900
      TTTGTCTAAGGTACATAACAAAGGTACGAGTGTTTTCTTGAGATAAAAATAGTGATTTCT
      LysGlnIleProCysIleValSerMetLeuThrLysGluLeuTyrPheTyrHisEnd

AATGGTTGGTTGGTGGTTTTTTTTAGTTTGTATGCCAAGTGAGAAGATGGTATATTTGGT
901   ---------+---------+---------+---------+---------+---------+  960
      TTACCAACCAACCACCAAAAAAAATCAAACATACGGTTCACTCTTCTACCATATAAACCA

ACTGTATTTCCCTCTCATTTTGACCTACTCTCATGCTGCAG
961   ---------+---------+---------+--         1001
      TGACATAAAGGGAGAGTAAAACTGGATGAGAGTACGACGTC
```

FIGURE 4B

LIGANDS FOR PHOSPHATASE BINDING ASSAY

CROSS-REFERENCE TO RELATED APPLICATIONS

This application claims benefit of Provisional 60/030,411 filed Nov. 4, 1996.

STATEMENT REGARDING FEDERALLY-SPONSORED R&D

Not Applicable.

REFERENCE TO MICROFICHE APPENDIX

Not Applicable.

FIELD OF THE INVENTION

This invention relates to the use of mutant phosphatase and protease enzymes in a competitive binding assay. Specific examples are the enzymes, tyrosine phosphatase and cysteine protease, e.g. Cathepsin K, and the assay specifically described is a scintillation proximity assay using a radioactive inhibitor to induce scintillation.

BACKGROUND OF THE INVENTION

The use of the scintillation proximity assay (SPA) to study enzyme binding and interactions is a new type of radioimmunoassay and is well known in the art. The advantage of SPA technology over more conventional radioimmunoassay or ligand-binding assays, is that it eliminates the need to separate unbound ligand from bound ligand prior to ligand measurement. See for example, *Nature*, Vol, 341, pp. 167–178 entitled "Scintillation Proximity Assay" by N. Bosworth and P. Towers, *Anal. Biochem.* Vol. 217, pp. 139–147 (1994) entitled "Biotinylated and Cysteine-Modified Peptides as Useful Reagents For Studying the Inhibition of Cathepsin G" by A. M. Brown, et al., *Anal. Biochem.* Vol. 223, pp. 259–265 (1994) entitled "Direct Measurement of the Binding of RAS to Neurofibromin Using Scintillation Proximity Assay" by R. H. Skinner et al. and *Anal. Biochem.* Vol. 230, pp. 101–107(1995) entitled "Scintillation Proximity Assay to Measure Binding of Soluble Fibronectin to Antibody-Captured alpha$_5$β$_1$ Integrin" by J. A. Pachter et al.

The basic principle of the assay lies in the use of a solid support containing a scintillation agent, wherein a target enzyme is attached to the support through, e.g., a second enzyme-antienzyme linkage. A known tritiated or I$^{125}$ iodinated binding agent, i.e., radioligand inhibitor ligand for the target enzyme is utilized as a control, which when bound to the active site in the target enzyme, is in close proximity to the scintillation agent to induce a scintillation signal, e.g., photon emission, which can be measured by conventional scintillation/radiographic techniques. The unbound tritiated (hot) ligand is too far removed from the scintillation agent to cause an interfering measurable scintillation signal and therefore does not need to be separated, e.g., filtration, as in conventional ligand-binding assays.

The binding of an unknown or potential new ligand (cold, being non-radioactive) can then be determined in a competitive assay versus the known radioligand, by measuring the resulting change in the scintillation signal which will significantly decrease when the unknown ligand also possesses good binding properties.

However, a problem arises when utilizing a target enzyme containing a cysteine group, having a free thiol linkage, —SH, (or present as —S$^-$) which is in the active site region or is closely associated with the active site and is important for enzyme-ligand binding. If the unknown ligand or mixture, e.g. natural product extracts, human body fluids, cellular fluids, etc. contain reagents which can alkylate, oxidize or chemically interfere with the cysteine thiol group such that normal enzyme-ligand binding is disrupted, then false readings will occur in the assay.

What is needed in the art is a method to circumvent and avoid the problem of cysteine interference in the scintillation proximity assay (SPA) procedure in enzyme binding studies.

SUMMARY OF THE INVENTION

We have discovered that by substituting serine for cysteine in a target enzyme, where the cysteine plays an active role in the wild-type enzyme-natural ligand binding process, usually as the catalytic nucleophile in the active binding site, a mutant is formed which can be successfully employed in a scintillation proximity assay without any active site cysteine interference.

This discovery can be utilized for any enzyme which contains cysteine groups important or essential for binding and/or catalytic activity as proteases or hydrolases and includes phosphatases, e.g., tyrosine phosphatases and proteases, e.g. cysteine proteases, including the cathepsins, i.e., Cathepsin K (O2) and the capsases.

Further, use of the mutant enzyme is not limited to the scintillation proximity assay, but can be used in a wide variety of known assays including colorimetric, spectrophotometric, ligand-binding assays, radioimmunoassays and the like.

We have furthermore discovered a new method of amplifying the effect of a binding agent ligand, e.g., radioactive inhibitor, useful in the assay by replacing two or more phosphotyrosine residues with 4-phosphono (difluoromethyl) phenylalanine (F$_2$Pmp) moieties. The resulting inhibitor exhibits a greater and more hydrolytically stable binding affinity for the target enzyme and a stronger scintillation signal.

By this invention there is provided a process for determining the binding ability of a ligand to a cysteine-containing wild-type enzyme comprising the steps of:

(a) contacting a complex with the ligand, the complex comprising a mutant form of the wild-type enzyme, in which cysteine, at the active site, is replaced with serine, in the presence of a known binding agent for the mutant enzyme, wherein the binding agent is capable of binding with the mutant enzyme to produce a measurable signal.

Further provided is a process for determining the binding ability of a ligand, preferably a non-radioactive (cold) ligand, to an active site cysteine-containing wild-type tyrosine phosphatase comprising the steps of:

(a) contacting a complex with the ligand, the complex comprising a mutant form of the wild-type enzyme, the mutant enzyme being PTP1B, containing the same amino acid sequence 1–320 as the wild type enzyme, except at position 215, in which cysteine is replaced with serine in the mutant enzyme, in the presence of a known radioligand binding agent for the mutant enzyme, wherein the binding agent is capable of binding with the mutant enzyme to produce a measurable beta radiation-induced scintillation signal.

Also provided is a new class of peptide binding agents selected from the group consisting of:

N-Benzoyl-L-glutamyl-[4-phosphono(difluoromethyl)]-L-phenylalanyl-[4-phosphono(difluoromethyl)]-L-phenylalanineamide (BzN-EJJ-CONH$_2$), where E is glutamic acid and J is 4-phosphono(difluoromethyl)]-L-phenylalanyl;

N-Benzoyl-L-glutamyl-[4-phosphono(difluoromethyl)]-L-phenylalanyl-[4-phosphono(difluoromethyl)]-L-phenylalanine amide;

N-Acetyl-L-glutamyl-[4-phosphono(difluoromethyl)]-L-phenylalanyl-[4-phosphono(difluoromethyl)]-L-phenylalanine amide;

L-Glutamyl-[4-phosphono(difluoromethyl)]-L-phenylalanyl-[4-phosphono-(difluoromethyl)]-L-phenylalanine amide;

L-Lysinyl-[4-phosphono(difluoromethyl)]-L-phenylalanyl-[4-phosphono-(difluoromethyl)]-L-phenylalanine amide;

L-Serinyl-[4-phosphono(difluoromethyl)]-L-phenylalanyl-[4-phosphono-(difluoromethyl)]-L-phenylalanine amide;

L-Prolinyl-[4-phosphono(difluoromethyl)]-L-phenylalanyl-[4-phosphono-(difluoromethyl)]-L-phenylalanine amide; and L-Isoleucinyl-[4-phosphono(difluoromethyl)]-L-phenylalanyl-[4-phosphono-(difluoromethyl)]-L-phenylalanine amide; and their tritiated and $I^{125}$ iodinated derivatives.

Further provided is a novel tritiated peptide, tritiated BzN-EJJ-CONH$_2$, being N-(3,5-Ditritio)benzoyl-L-glutamyl-[4-phosphono(difluoromethyl)]-L-phenylalanyl-[4-phosphono(difluoromethyl)]-L-phenylalanineamide, wherein E as used herein is glutamic acid and J, as used herein, is the (F$_2$Pmp) moiety, (4-phosphono (difluoromethyl)-phenylalanyl).

Furthermore there is provided a process for increasing the binding affinity of a ligand for a tyrosine phosphatase or cysteine protease comprising introducing into the ligand two or more 4-phosphono(difluoromethyl)-phenylalanine groups; also provided is the resulting disubstituted ligand.

In addition there is provided a complex comprised of:

(a) a mutant form of a wild-type enzyme, in which cysteine, necessary for activity in the active site, is replaced with serine and is attached to:

(b) a solid support.

BRIEF DESCRIPTION OF THE DRAWINGS

FIGS. 2(A and B) illustrates the DNA and amino acid sequences for PTP1B tyrosine phosphatase enzyme, truncated to amino acid positions 1–320. (Active site cysteine at position 215 is in bold and underlined).

FIGS. 3(A, B and C) illustrates the DNA and amino acid sequences for Cathepsin K. The upper nucleotide sequence represents the cathepsin K cDNA sequence which encodes the cathepsin K preproenzyme (indicated by the corresponding three letter amino acid codes). Numbering indicates the cDNA nucleotide position. The underlined amino acid is the active site Cys$^{139}$ residue that was mutated to either Ser or Ala.

FIGS. 4(A and B) illustrates the DNA and amino acid sequences for the capsase, apopain. The upper nucleotide sequence represents the apopain (CPP32) cDNA sequence which encodes the apopain proenzyme (indicated by the corresponding three letter amino acid codes). Numbering indicates the cDNA nucleotide position. The underlined amino acid is the active site Cys$^{163}$ residue that was mutated to Ser.

DETAILED DESCRIPTION OF THE INVENTION

Figure 1:
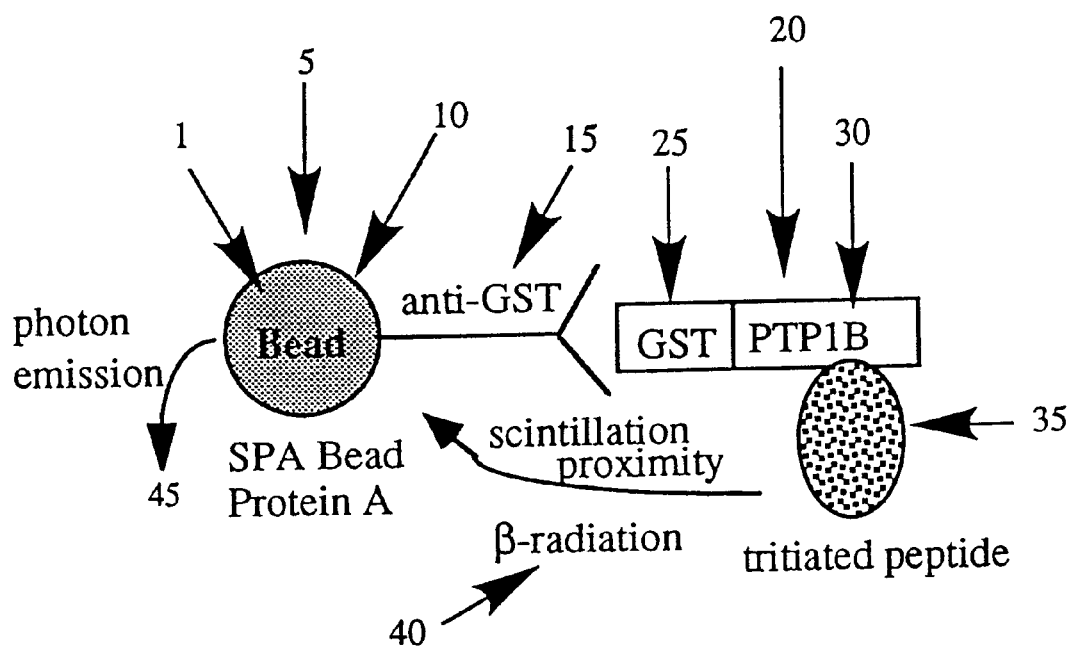
FIG. 1 illustrates the main elements of the invention including the scintillation agent 1, the supporting (fluomicrosphere) bead 5, the surface binding Protein A 10, the linking anti-GST enzyme 15, the fused enzyme construct 20, the GST enzyme 25, the mutant enzyme 30, the tritiated peptide inhibitor 35, the beta radiation emission 40 from the radioactive peptide inhibitor 35 and the emitted light 45 from the induced scintillation.

The theory underlying the main embodiment of the invention can be readily seen and understood by reference to FIG. 1.

Scintillation agent 1 is incorporated into small (yttrium silicate or PVT fluomicro-spheres, AMERSHAM) beads 5 that contain on their surface immunosorbent protein A 10. The protein A coated bead 5 binds the GST fused enzyme construct 20, containing GST enzyme 25 and PTP1B mutant enzyme 30, via anti-GST enzyme antibody 15. When the radioactive e.g., tritiated, peptide 35 is bound to the mutant phosphatase enzyme 30, it is in close enough proximity to the bead 5 for its beta emission 40 (or Auger electron emission in the case of $I^{125}$) to stimulate the scintillation agent 1 to emit light (photon emission) 45. This light 45 is measured as counts in a beta plate counter. When the tritiated peptide 35 is unbound it is too distant from the scintillation agent 1 and the energy is dissipated before reaching the bead 5, resulting in low measured counts. Non-radioactive ligands which compete with the tritiated peptide 35 for the same binding site on the mutant phosphatase enzyme 3 will remove and/or replace the tritiated peptide 35 from the mutant enzyme 30 resulting in lower counts from the uncompeted peptide control. By varying the concentration of the unknown ligand and measuring the resulting lower counts, the inhibition at 50%(IC$_{50}$) for ligand binding to the mutant enzyme 30 can be obtained. This then is a measure of the binding ability of the ligand to the mutant enzyme and the wild-type enzyme.

The term "complex" as used herein refers to the assembly containing the mutant enzyme. In its simplest embodiment, the complex is a solid support with the mutant enzyme attached to the surface of the support. A linker can also be employed. As illustrated in FIG. 1, the complex can further comprise a bead (fluopolymer), anti-enzyme GST/enzyme GST-mutant enzyme-PTP1 linking construct, immunosorbent protein A, and scintillation agent. In general, the complex requires a solid support (beads, immunoassay column of e.g., Al$_2$O$_3$, or silica gel) to which the mutant enzyme can be anchored or tethered by attachment through a suitable linker, e.g., an immunosorbent (e.g., Protein A, Protein G, anti-mouse, anti-rabbit, anti-sheep) and a linking assembly, including an enzyme/anti-enzyme construct attached to the solid support.

The term "cysteine-containing wild-type enzyme", as used herein, includes all native or natural enzymes, e.g., phosphatases, cysteine proteases, which contain cysteine in the active site as the active nucleophile, or contain cysteine clearly associated with the active site that is important in binding activity.

The term "binding agent" as used herein includes all ligands (compounds) which are known to be able to bind with the wild-type enzyme and usually act as enzyme inhibitors. The binding agent carries a signal producing agent, e.g., radionuclide, to initiate the measurable signal. In the SPA assay the binding agent is a radioligand.

The term "measurable signal" as used herein includes any type of generated signal, e.g., radioactive, colorimetric, photometric, spectrophotometric, scintillation, which is produced when binding of the radioligand binding agent to the mutant enzyme.

The present invention assay further overcomes problems encountered in the past, where compounds were evaluated by their ability to affect the reaction rate of the enzyme in the phosphatase activity assay. However this did not give direct evidence that compounds were actually binding at the active site of the enzyme. The herein described invention binding assay using a substrate analog can determine directly whether the mixtures of natural products can irreversibly modify the active site cysteine in the target enzyme resulting in inhibition of the enzymatic activity. To overcome inhibition by these contaminates in the phosphatase assay, a mutated Cys(215) to Ser(215) form of the tyrosine phosphatase PTP1B was cloned and expressed resulting in a catalytically inactive enzyme. In general, replacement of cysteine by serine will lead to a catalytically inactive or substantially reduced activity mutant enzyme.

PTP1B is the first protein tyrosine phosphatase to be purified to near homogeneity {Tonks et al. *JBC* 263, 6731–6737 (1988)} and sequenced by Charbonneau et al. *PNAS* 85, 7182–7186 (1988). The sequence of the enzyme showed substantial homology to a duplicated domain of an abundant protein present in hematopoietic cells variously referred to as LCA or CD45. This protein was shown to possess tyrosine phosphatase activity {Tonks et al. *Biochemistry* 27, 8695–8701 (1988)}. Protein tyrosine phosphatases have been known to be sensitive to thiol oxidizing agents and alignment of the sequence of PTP1B with subsequently cloned Drosophila and mammalian tyrosine phosphatases pointed to the conservation of a Cysteine residue {(M. Strueli et al. *Proc. Nat'l Acad USA*, Vol. 86, pp. 8698–7602 (1989)} which when mutated to Ser inactivated the catalytic activity of the enzymes. Guan et al.(1991) {J.B.C. Vol. 266, 17926–17030, 1991} cloned the rat homologue of PTP1B, expressed a truncated version of the protein in bacteria, purified and showed the Cys at position 215 is the active site residue. Mutation of the $Cys^{215}$ to $Ser^{215}$ resulted in loss of catalytic activity. Human PTP1B was cloned by Chernoff et al. Proc. Natl. Acad. Sci. USA 87, 2735–2739 (1990).

Work leading up to the development of the substrate analog $BzN-EJJ-CONH_2$ for PTP1B was published by T. Burke et al. *Biochem. Biophys. Res. Comm.* 205, pp. 129–134 (1994) with the synthesis of the hexamer peptide containing the phosphotyrosyl mimetic $F_2Pmp$. We have incorporated the ($F_2Pmp$) moiety (4-phosphono-(difluoromethyl)phenylalanyl) into various peptides that led to the discovery of $BzN-EJJ-CONH_2$, (where E is glutamic acid and J as used herein is the $F_2Pmp$ moiety) an active (5 nM) inhibitor of PTP1B. This was subsequently tritiated giving the radioactive substrate analog required for the binding assay.

The mutated enzyme, as the truncated version, containing amino acids 1–320 (see FIG. 2), has been demonstrated to bind the substrate analog $Bz-NEJJ-CONH_2$ with high affinity for the first time. The mutated enzyme is less sensitive to oxidizing agents than the wild-type enzyme and provides an opportunity to identify novel inhibitors for this family of enzymes. The use of a mutated enzyme to eliminate interfering contaminates during drug screening is not restricted to the tyrosine phosphatases and can be used for other enzyme binding assays as well.

Other binding assays exist in the art in which the basic principle of this invention can be utilized, namely, using a mutant enzyme in which an important and reactive cysteine important for activity can modified to serine (or a less reactive amino acid) and render the enzyme more stable to cysteine modifying reagents, such as alkylating and oxidizing agents. These other ligand-binding assays include, for example, colorimetric and spectrophotometric assays, e.g. measurement of produced color or fluorescence, phosphorescence (e.g. ELISA, solid absorbant assays) and other radioimmunoassays in which short or long wave light radiation is produced, including ultraviolet and gamma radiation).

Further, the scintillation proximity assay can also be practiced without the fluopolymer support beads (AMERSHAM) as illustrated in FIG. 1. For example, Scintistrips® are commercially available (Wallac Oy, Finland) and can also be employed as the scintillant-containing solid support for the mutant enzyme complex as well as other solid supports which are conventional in the art.

The invention assay described herein is applicable to a variety of cysteine-containing enzymes including protein phosphatases, proteases, lipases, hydrolases, and the like.

The cysteine to serine transformation in the target enzyme can readily be accomplished by analogous use of the molecular cloning technique for $Cys^{215}$ to $Ser^{215}$ described in the below-cited reference by M. Strueli et al., for PTP1B and is hereby incorporated by reference for this particular purpose.

A particularly useful class of phosphatases is the tyrosine phosphatases since they are important in cell function. Examples of this class are: PTP1B, LCA, LAR, DLAR, DPTP(See Strueli et al., below). Ligands discovered by this assay using, for example, PTP1B can be useful, for example, in the treatment of diabetes and immunosuppression.

A useful species is PTP1B, described in *Proc. Nat'l Acad USA*, Vol. 86, pp. 8698–7602 by M. Strueli et al. and *Proc. Nat'l Acad Sci. USA*, Vol 87, pp. 2735–2739 by J. Chernoff et al.

Another useful class of enzymes is the proteases, including cysteine proteases (thiol proteases), cathepsins and capsases.

The cathepsin class of cysteine proteases is important since Cathepsin K (also termed Cathepsin 02, see *Biol. Chem. Hoppe-SeyZer*, Vol. 376 pp. 379–384, June 1995 by D. Bromme et al.) is primarily expressed in human osteoclasts and therefore this invention assay is useful in the study and treatment of osteoporosis. See U.S. Pat. No. 5,501,969 (1996) to Human Genome Sciences for the sequence, cloning and isolation of Cathepsin K (O2). See also *J. Biol. Chem.* Vol. 271, No. 21, pp. 12511–12516 (1996) by F. Drake et al. and *Biol. Chem. Hoppe-Seyler*, Vol. 376, pp. 379–384(1985) by D. Bromine et al., supra.

Examples of the cathepsins include Cathepsin B, Cathepsin G, Cathepsin J, Cathepsin K(O2), Cathesin L, Cathepsin M, Cathepsin S.

The capsase family of cysteine proteases are other examples where the SPA technology and the use of mutated enzymes can be used to determine the ability of unknown compounds and mixtures of compounds to compete with a radioactive inhibitor of the enzyme. An active site mutant of Human Apopain CPP32 (capsase-3) has been prepared. The active site thiol mutated enzymes are less sensitive to oxidizing agents and provide an opportunity to identify novel inhibitors for this family of enzymes.

Examples of the capsase family include: capsase-1(ICE), capsase-2 (ICH-1), capsase-3 (CPP32, human apopain, Yama), capsase-4($ICE_{rel}$-11, TX, ICH-2), capsase-5($ICE_{rel}$-111, TY), capsase-6(Mch2), capsase-7(Mch3, ICE-LAP3, CMH-1), capsase-8(FLICE, MACH, Mch5), capsase-9 (ICE-LAP6, Mch6) and capsase-10(Mch4).

Substitution of the cysteine by serine (or by any other amino acid which lowers the activity to oxidizing and alkylating agents, e.g., alanine) does not alter the binding ability of the mutant enzyme to natural ligands. The degree of binding, i.e., binding constant, may be increased or decreased. The catalytic activity of the mutant enzyme will, however, be substantially decreased or even completely eliminated. Thus, natural and synthetic ligands which bind to the natural wild-type enzyme will also bind to the mutant enzyme.

Substitution. by serine for cysteine also leads to the mutant enzyme which has the same qualititative binding ability as the natural enzyme but is significantly reduced in catalytically activity. Thus, this invention assay is actually measuring the true binding ability of the test ligand.

The test ligand described herein is a new ligand potentially useful in drug screening purposes and its mode of action is to generally function as an inhibitor for the enzyme.

The binding agent usually is a known ligand used as a control and is capable of binding to the natural wild-type enzyme and the mutant enzyme employed in the assay and is usually chosen as a known peptide inhibitor for the enzyme.

The binding agent also contains a known signal-producing agent to cause or induce the signal in the assay and can be an agent inducing e.g., phosphorescence or fluorescence (ELISA), color reaction or a scintillation signal.

In the instant embodiment, where the assay is a scintilation assay, the signal agent is a radionuclide, i.e., tritium, $I^{125}$, which induces the scintillant in the solid support to emit measurable light radiation, i.e., photon emission, which can be measured by using conventional scintillation and beta radiation counters.

We have also discovered that introducing two or more 4-phosphonodifluoromethyl phenylalanine ($F_2Pmp$) groups into a known binding agent greatly enhances the binding affinity of the binding agent to the enzyme and improves its stability by rendering the resulting complex less susceptible to hydrolytic cleavage.

A method for introducing one $F_2Pmp$ moiety into a ligand is known in the art and is described in detail in *Biochem. Biophys. Res. Comm.* Vol. 204, pp. 129–134 (1994) hereby incorporated by reference for this particular purpose.

As a result of this technology we discovered a new class of ligands having extremely good binding affinity for PTP1B. These include:

N-Benzoyl-L-glutamyl-[4-phosphono(difluoromethyl)]-L-phenylalanyl-[4-phosphono(difluoromethyl)]-L-phenylalanine amide, N-Acetyl-L-glutamyl-[4-phosphono(difluoromethyl)]-L-phenylalanyl-[4-phosphono(difluoromethyl)]-L-phenylalanine amide, L-Glutamyl-[4-phosphono(difluoromethyl)]-L-phenylalanyl-[4-phosphono(difluoromethyl)]-L-phenylalanine amide, L-Lysinyl-[4-phosphono(difluoromethyl)]-L-phenylalanyl-[4-phosphono(difluoromethyl)]-L-phenylalanine amide, L-Serinyl-[4-phosphono(difluoromethyl)]-L-phenylalanyl-[4-phosphono(difluoromethyl)]-L-phenylalanine amide, L-Prolinyl-[4-phosphono(difluoromethyl)]-L-phenylalanyl-[4-phosphono(difluoromethyl)]-L-phenylalanine amide, and L-Isoleucinyl-[4-phosphono(difluoromethyl)]-L-phenylalanyl-[4-phosphono(difluoromethyl)]-L-phenylalanine amide.

A useful ligand in the series is Bz-NEJJ-CONH$_2$, whose chemical name is: N-Benzoyl-L-glutamyl-[4-phosphono(difluoro-methyl)]-L-phenylalanyl-[4-phosphono(difluoromethyl)]-L-phenyl-alanineamide, and its tritiated form, N-(3,5-Ditritio)benzoyl-L-glutamyl-[4-phosphono(difluoromethyl)]-L-phenylalanyl-[4-phosphono(dilfuoromethyl)]-L-phenylalanineamide.

Synthesis of both cold and hot ligands is described in the Examples.

The following Examples are illustrative of carrying out the invention and should not be construed as being limitations on the scope or spirit of the instant invention.

EXAMPLES

1. Preparation of PTP1B Truncate (Amino Acid Sequence from 1–320 and Fused GST-PTP1B Construct An *E. coli* culture carrying a PET plasmid expressing the full length PTP1B protein was disclosed in J. Chernoff et al. *Proc Natl. Acad. Sci. USA*, 87, pp. 2735–2739, (1990). This was modified to a truncated PTP1B enzyme complex containing the active site with amino acids 1–320 inclusive, by the following procedure:

The full length human PTP-1B cDNA sequence (published in J. Chernoff et al., PNAS, USA, supra) cloned into a PET vector was obtained from Dr. Raymond Erickson (Harvard University). The PTP-1B cDNA sequence encoding amino acids 1–320 (Seq. ID No. 1) was amplified by PCR using the full length sequence as template. The 5' primer used for the amplification included a Barn HI site at the 5' end and the 3' primer had an Eco RI site at the 3' end. The amplified fragment was cloned into pCR2 (Invitrogen) and sequenced to insure that no sequence errors had been introduced by Taq polymerase during the amplification. This sequence was released from pCR2 by a Bam HI/Eco RI digest and the PTP-1B cDNA fragment ligated into the GST fusion vector pGEX-2T (Pharmacia) that had been digested with the same enzymes. The GST-PTP-1B fusion protein expressed in *E. Coli* has an active protein tyrosine phosphatase activity. This same 1–320 PTP-1B sequence (Seq. ID No. 1) was then cloned into the expression vector pFLAG-2, where FLAG is the octa-peptide Asp-TyrLysAspAspAspAspLys. This was done by releasing the PTP-1B sequence from the pGEX-2T vector by Nco I/Eco RI digest, filling in the ends of this fragment by Kienow and blunt-end ligating into the blunted Eco RI site of pFLAG2. Site-directed mutagenesis was performed on pFLAG2-PTP-1B plasmid using the Chameleon (Stratagene) double-stranded mutagenesis kit from Stratagene, to replaced the active-site Cys-215 with serine. The mutagenesis was carried out essentially as described by the manufacturer and mutants identfed by DNA sequencing. The FLAG-PTP-1B Cys215Ser mutant (Seq. ID No. 7) was expressed, purified and found not to have any phosphatase activity. The GDT-PTP-1B Cys$^{215}$Ser mutant was made using the mutated Cys$^{215}$Ser sequence of PTP-1B already cloned into pFLAG2, as follows. The pFLAG2-PTP-1B Cys$^{215}$Ser plasmid (Seq. ID No. 7) was digested with Sal I (3' end of PTP-1B sequence), filled in using Klenow polymerase (New England Biolabs), the enzymes were heat inactivated and the DNA redigested with Bgl II. The 500 bp 3' PTP-1B cDNA fragment which is released and contains the mutated active site was recovered. The pGEX-2T-PTP-1B plasmid was digested with Eco RI (3' end of PTP-1B sequence), filled in by Klenow, phenol/chloroform extracted and ethanol precipitated. This DNA was then digested with Bgl II, producing two DNA fragments a 500 bp 3' PTP-1B cDNA fragment that contains the active site and a 5.5 Kb fragment containing the pGEX-2T vector plus the 5' end of PTP-1B. The 5.5 Kb pGEX-2T 5' PTP-1B fragment was recovered and ligated with the 500 bp Bgl II/Sal I fragment containing the mutated active site. The ligation was transformed into bacteria (type DH5α, G) and clones containing the mutated active site sequence identified by sequencing. The GST-PTP-1B Cys$^{215}$Ser mutant was overexpressed, purified and found not to have any phosphatase activity.

2. Preparation of Tritiated Bz-NEJJ-CONH$_2$

This compound can be prepared as outlined in Scheme 1, below, and by following the procedures:
Synthesis of N-Benzoyl-L-glutamyl-[4-phosphono(difluoromethyl)]-L-phenylalanyl-[4-phosphono(difluoromethyl)]-L-phenylalanineamide (BzN-EJJ-CONH$_2$)

1.0 g of TentaGel® S RAM resin (RAPP polymer, ~0.2 mmol/g) as represented by the shaded bead in Scheme 1, was treated with piperidine (3 mL) in DMF (5 mL) for 30 min. The resin (symbolized by the circular P, containing the remainder of the organic molecule except the amino group) was washed successively with DMF (3×10 mL) and CH$_2$Cl$_2$ (10 mL) and air dried. A solution of DMF (5 mL), N$^{28}$-Fmoc-4-[diethylphosphono-(difluoromethyl)]-L-phenylalanine (350 mg), where Fmoc is 9-fluorenylmethoxycarbonyl, and O-(7-azabenzotriazol-1-yl)-1,1,3,3-tetramethyluranium hexafluorphosphate, (acronym being HATU, 228 mg) was treated with diisopropyl-ethylamine (0.21 mL) and, after 15 min., was added to the resin in 3 mL of DMF. After 1 h, the resin was washed successively with DMF (3×10 mL) and CH$_2$Cl$_2$ (10 mL) and air dried. The sequence was repeated two times, first using N$^\infty$-Fmoc-4-[diethylphosphono-(difluoromethyl)]-L-phenylalamine and then using N-Fmoc-L-glutamic acid gamma-t-butyl ester. After the final coupling, the resin bound tripeptide was treated with a mixture of piperidine (3 mL) in DMF (5 mL) for 30 min. and was then washed successively with DMF (3×10 mL) and CH$_2$Cl$_2$ (10 mL) and air dried.

To a solution of benzoic acid (61 mg) and HATU (190 mg) in DMF (1 mL) was added diisopropylethylamine (0.17 mL) and, after 15 min. the mixture was added to a portion of the resin prepared above (290 mg) in 1 mL DMF. After 90 min. the resin was washed successively with DMF (3×10 mL) and CH$_2$Cl$_2$ (10 mL) and air dried. The resin was treated with 2 mL of a mixture of TFA: water (9:1) and 0.05 mL of triisopropylsilane (TIPS-H) for 1 h. The resin was filtered off and the filtrate was diluted with water (2 mL) and concentrated in vacuo at 35° C. The residue was treated with 2.5 mL of a mixture of TFA:DMS:TMSOTf (5:3:1) and 0.05 mL of TIPS-H, and stirred at 25° C. for 15 h. (TFA is trifluoroacetic acid, DMS is dimethyl sulfate, TMSOTf is trimethylsilyl trifluoromethanesulfonate).

The desired tripeptide, the title compound, was purified by reverse phase HPLC (C18 column, 25×100 mm) using a mobile phase gradient from 0.2% TFA in water to 50/50 acetonitrile/0.2% TFA in water over 40 min. and monitoring at 230 nm. The fraction eluting at approximately 14.3 min. was collected, concentrated and lyophylized to yield the title compound as a white foam.

Synthesis of N-(3,5-Ditritio)benzoyl-L-glutamyl-[4-phosphono(difluoromethyl)]-L-phenylalanyl-[4-phosphono(dilfuoromethyl)]-L-phenylalanineamide The above procedure described for the preparation of BzN-EJJ-CONH$_2$ was repeated, but substituting 3,5-dibromobenzoic acid for benzoic acid. After HPLC purification as before, except using a gradient over 30 min. and collecting the fraction at approximately 18.3 min., the dibromo containing tripeptide was obtained as a white foam.

A portion of this material (2 mg) was dissolved in methanol/triethylamine (0.5 mL, 4/1), 10% Pd-C (2 mg) was added, and the mixture stirred under an atmosphere of tritium gas for 24 h. The mixture was filtered through celite, washing with methanol and the filtrate was concentrated. The title compound was obtained after purification by semi-preparative HPLC using a C18 column and an isocratic mobile phase of acetonitrile/0.2% TFA in water (15:100). The fraction eluting at approximately 5 min. was collected and concentrated in vacuo. The title compound was dissolved in 10 mL of methanol/water (9:1) to provide a 0.1 mg/mL solution of specific activity 39.4 Ci/mmol.

Scheme 1

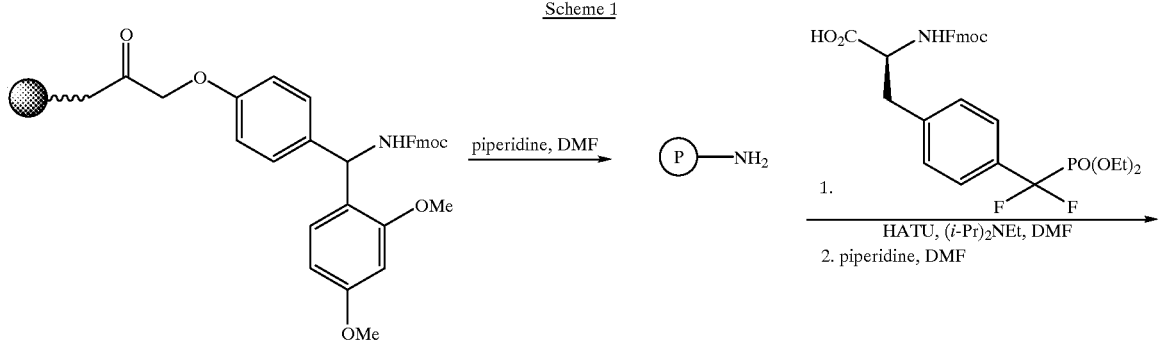

TentaGel® S RAM polymer

-continued

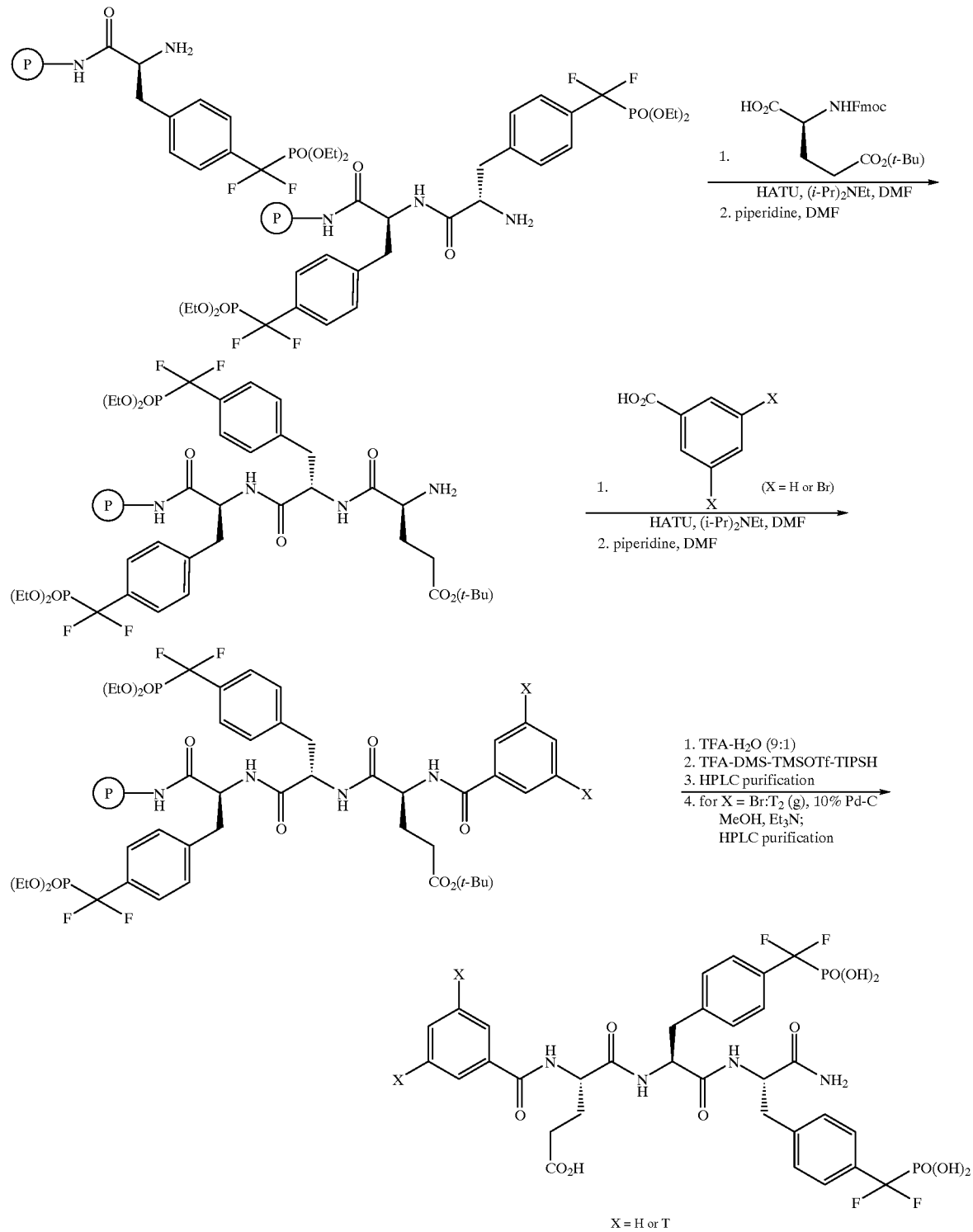

By following the above described procedure for BzN-EJJ-CONH₂, the following other peptide inhibitors were also similarly prepared:

N-Benzoyl-L-glutamyl-[4-phosphono(difluoromethyl)]-L-phenylalanyl-[4-phosphono(difluoromethyl)]-L-phenylalanine amide, N-Acetyl-L-glutamyl-[4-phosphono(difluoromethyl)]-L-phenylalanyl-[4-phosphono(difluoromethyl)]-L-phenylalanine amide, L-Glutamyl-[4-phosphono(difluoromethyl)]-L-phenylalanyl-[4-phosphono(difluoromethyl)]-L-phenylalanine amide, L-Lysinyl-[4-phosphono(difluoromethyl)]-L-phenylalanyl-[4-phosphono(difluoromethyl)]-L-phenylalanine amide, L-Serinyl-[4-phosphono(difluoromethyl)]-L-phenylalanyl-[4-phosphono(difluoromethyl)]-L-phenylalanine amide, L-Prolinyl-[4-phosphono(difluoromethyl)]-L-phenylalanyl-[4-phosphono(difluoromethyl)]-L-phenylalanine amide, and L-Isoleucinyl-[4-phosphono(difluoromethyl)]-L-phenylalanyl-[4-phosphono(difluoromethyl)]-L-phenylalanine amide.

4. Phosphatase Assay Protocol

Materials

EDTA—ethylenediaminetetraacetic acid (Sigma)

DMH—N,N'-dimethyl-N,N'-bis(mercaptoacetyl)-hydrazine (synthesis published in *J. Org. Chem.* 56, pp. 2332–2337,(1991) by R. Singh and G. M. Whitesides and can be substituted with DTT—dithiothreitol Bistris—2,2-bis(hydroxymethyl)2,2',2"-nitrilotriethanol-(Sigma) Triton X-100—octylphenolpoly(ethyleneglycolether) 10 (Pierce)

Antibody: Anti-glutathione S-transferase rabbit (H and L) fraction (Molecular Probes)

Enzyme: Human recombinant PTP1B, containing amino acids 1–320, (Seq. ID No. 1) fused to GST enzyme (glutathione S-transferase) purified by affinity chromatography. Wild type (Seq. ID No. 1) contains active site cysteine (215), whereas mutant (Seq. ID No. 7) contains active site serine(215).

Tritiated peptide: Bz-NEJJ-CONH$_2$, Mwt. 808, empirical formula, $C_{32}H_{32}T_2O_{12}P_2F_4$

| Stock Solutions | |
|---|---|
| (10X) Assay Buffer | 500 mM Bistris (Sigma); pH 6.2, |
| | MW = 209.2 |
| | 20 mM EDTA (GIBCO/BRL) |
| | Store at 4° C. |
| Prepare fresh daily: | |
| Assay Buffer (1X) | 50 mM Bistris |
| (room temp.) | 2 mM EDTA |
| | 5 mM DMH (MW = 208) |
| Enzyme Dilution | |
| Buffer (keep on ice) | 50 mM Bistris |
| | 2 mM EDTA |
| | 5 mMDMH |
| | 20% Glycerol (Sigma) |
| | 0.01 mg/ml Triton X-100 (Pierce) |

| -continued | |
|---|---|
| Antibody Dilution | |
| Buffer (keep on ice) | 50 mM Bistris |
| | 2 mM EDTA |

IC$_{50}$ Binding Assay Protocol

Compounds (ligands) which potentially inhibit the binding of a radioactive ligand to the specific phosphatase are screened in a 96-well plate format as follows:

To each well is added the following solutions @ 25° C. in the following chronological order:

1. 110 μl of assay buffer.

2. 10 μl. of 50 nM tritiated BzN-EJJ-CONH$_2$ in assay buffer (1X) @ 25° C.

3. 10 μl. of testing compound in DMSO at 10 different concentrations in serial dilution (final DMSO, about 5% v/v) in duplicate @ 25° C.

4. 10 μl. of 3.75 μg/ml purified human recombinant GST-PTP1B in enzyme dilution buffer.

5. The plate is shaken for 2 minutes.

6. 10 μl. of 0.3 μg/ml anti-glutathione S-transferase (anti-GST) rabbit IgG (Molecular Probes) diluted in antibody dilution buffer @ 25° C.

7. The plate is shaken for 2 minutes.

8. 50 μl. of protein A-PVT SPA beads (Amersham) @ 25° C.

9. The plate is shaken for 5 minutes. The binding signal is quantified on a Microbeta 96-well plate counter.

10. The non-specific signal is defined as the enzyme-ligand binding in the absence of anti-GST antibody.

11. 100% binding activity is defined as the enzyme-ligand binding in the presence of anti-GST antibody, but in the absence of the testing ligands with the non-specific binding subtracted.

12. Percentage of inhibition is calculated accordingly.

13. IC$_{50}$ value is approximated from the non-linear regression fit with the 4-parameter/multiple sites equation (described in: "Robust Statistics", New York, Wiley, by P. J. Huber (1981) and reported in nM units.

14. Test ligands (compounds) with larger than 90% inhibition at 10 μM are defined as actives.

The following Table I illustrates typical assay results of examples of known compounds which competitively inhibit the binding of the binding agent, BzN-EJJ-CONH2.

Examples of known compounds which competitively inhibit the binding of L-783,016
Typical Assay Results
GST-PTP1B SPA Binding Assay with Non-Mutated (Cys215) and Mutated enzyme (Ser215)

| Compound | L-Number | Structure | Non-Mutated | Mutated |
|---|---|---|---|---|
| Control: | | | | |
| Tripeptide (F2PMP)2 | L-783016-000P001 | 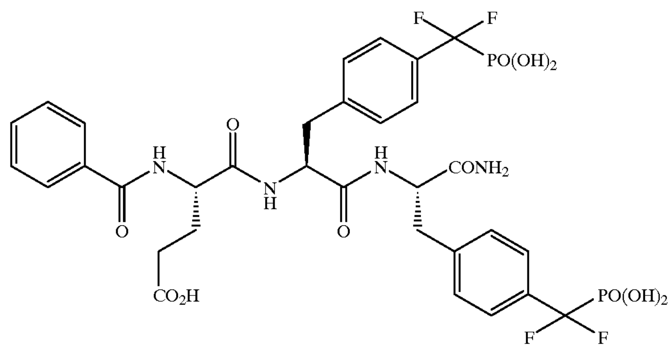 | 14 nM | 8 nM |
| DADE (F2PMP)L hexapeptide (T. Burke et al, Biochem. Biophys. Res. Comm. 204, 129, (1994) | | 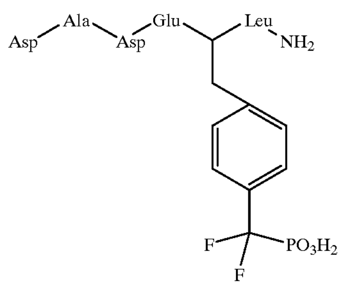 | 400 nM | 100 nM |
| SH-specific binding: | | | | |
| Vanadate | | 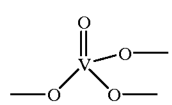 | 2 $\mu$M | >100 $\mu$M |
| Insulin Receptor Peptide | L-791352-000D001 | 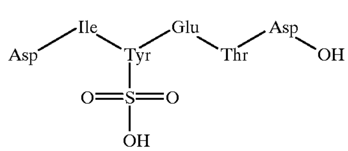 | 17 $\mu$M | 70 $\mu$M |
| Potential Oxidizing agents: | | | | |
| Hydrogen peroxide | | H2O2 | 90% at 83 $\mu$M | 0% at 83 $\mu$M |
| Quinone | L-289196-000P001 | 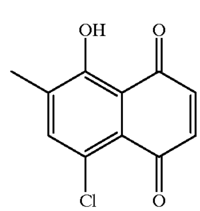 | 4 $\mu$M | >100 $\mu$M |
| Potential Alkylating agents: | | | | |

-continued

Examples of known compounds which competitively inhibit the binding of L-783,016
Typical Assay Results
GST-PTP1B SPA Binding Assay with Non-Mutated (Cys215) and Mutated enzyme (Ser215)

Imine  L-280684-000C001

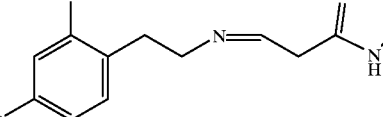

67% at 2 µM    10% at 2 µM

| | | | | | | | conc. L-783016-000P nM | | | | |
|---|---|---|---|---|---|---|---|---|---|---|---|
| no antibody (− control) | antibody (+ control) | 250 | 125 | 62.5 | 31.25 | 15.625 | 7.813 | 3.906 | 1.953 | 0.977 | 0.488 |
| | | | Raw Data, Counts (dpm) (duplicates) | | | | | | | | |
| dyne 252 | 5652 | 288 | 873 | 757 | 1550 | 2775 | 3367 | 4743 | 5220 | 5454 | 5384 |
| dpm 304 | 6380 | 273 | 588 | 1109 | 1337 | 2525 | 4165 | 4838 | 5581 | 5781 | 6211 |
| | | % Inhibition (1-(dpm-average no antibody)/(average antibody-average no antibody)) * 100 | | | | | | | | | |
| % Inh 100 | 5 | 100 | 90 | 92 | 78 | 56 | 45 | 21 | 12 | 8 | 9 |
| % Inh 100 | −8 | 100 | 95 | 85 | 81 | 60 | 30 | 19 | 6 | 2 | −5 |

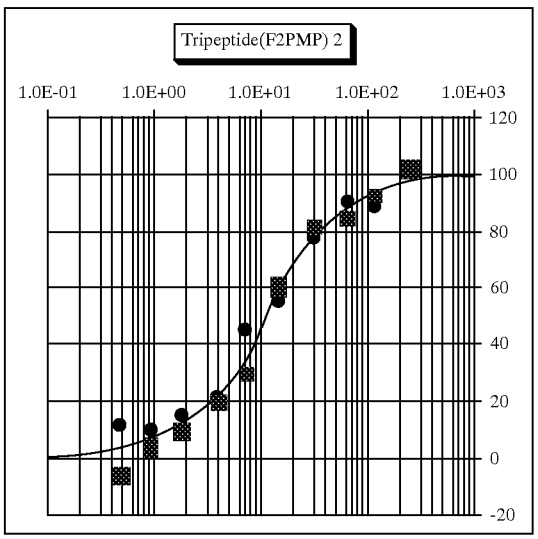

Preparation of Cathepsin K(O2) Mutant (CAT-K Mutant)

Cathepsin K is a prominent cysteine protease in human osteoclasts and is believed to play a key role in osteoclast-mediated bone resorption. Inhibitors of cathepsin K will be useful for the treatment of bone disorders (such as osteoporosis) where excessive bone resorption occurs. Cathepsin K is synthesized as a dormant preproenzyme (Seq. ID No. 4). Both the pre-domain (Met$^1$-Ala$^{15}$) and the prodomain (Leu$^{16}$-Arg$^{114}$) must be removed for full catalytic activity. The mature form of the protease (Ala$^{115}$-Met$^{329}$) contains the active site Cys residue (Cys$^{139}$).

The mature form of cathepsin K is engineered for expression in bacteria and other recombinant systems as a Met Ala$^{115}$-Met$^{329}$ construct by PCR-directed template modification of a clone that is identified. Epitope-tagged variants are also generated: (Met[FLAG]Ala$^{115}$-Met$^{329}$ and Met Ala$^{115}$-Met$^{329}$[FLAG]; where FLAG is the octa-peptide AspTyrLysAspAspAspAspLys). For the purpose of establishing a binding assay, several other constructs are generated including Met[FLAG]Ala$^{115}$-[Cys$^{139}$ to Ser$^{139}$]-Met$^{329}$ and Met Ala$^{115}$-[Cys$^{139}$ to Ser$^{139}$]-Met$^{329}$[FLAG] (where the active site Cys is mutated to a Ser residue), and Met [FLAG]Ala$^{115}$-[Cys$^{139}$ to Ala$^{139}$]-Met$^{329}$ and Met Ala$^{115}$-[Cys$^{139}$ to Ala$^{139}$]-Met$^{329}$[FLAG] (where the active site Cys is mutated to an Ala residue). In all cases, the resulting re-engineered polypeptides can be used in a binding assay by tethering the mutated enzymes to SPA beads via specific anti-FLAG antibodies that are commercially available (IDI-KODAK). Other epitope tags, GST and other fusions can also be used for this purpose and binding assay formats other than SPA can also be used. Ligands based on the prefered substrate for cathepsin K (e.g. Ac-P$_2$-P$_1$, Ac-P$_2$-P$_1$-aldehydes, Ac-P$_2$-P$_1$-ketones; where P1 is an amino acid with a hydrophilic side chain, preferably Arg or Lys, and P2 is an amino acid with a small hydrophobic side chain, preferably Leu, Val or Phe) are suitable in their radiolabeled (tritiated) forms for SPA-based binding assays. Similar binding assays can also be established for other cathepsin family members.

Preparation of Apopain (capsase-3) Mutant

Apopain is the active form of a cysteine protease belonging to the capsase superfamily of ICE/CED-3 like enzymes. It is derived from a catalytically dormant proenzyme that contains both the 17 kDa large subunit (p17) and 12 kDa (p12) small subunit of the catalytically active enzyme within a 32 kDa proenzyme polypeptide (p32). Apopain is a key mediator in the effector mechanism of apoptotic cell death and modulators of the activity of this enzyme, or structurally-related isoforms, will be useful for the therapeutic treatment of diseases where inappropriate apoptosis is prominent, e.g., Alzheimer's disease.

The method used for production of apopain involves folding of active enzyme from its constituent p17 and p12 subunits which are expressed separately in E. coli. The apopain p17 subunit ($Ser^{29}$-$Asp^{175}$) and p12 subunit ($Ser^{176}$-$His^{277}$) are engineered for expression as $MetSer^{29}$-$Asp^{175}$ and $MetSer^{176}$-$His^{277}$ constructs, respectively, by PCR-directed template modification. For the purpose of establishing a binding assay, several other constructs are generated, including a $MetSer^{29}$-[$Cys^{163}$ to $Ser^{163}$]-$Asp^{175}$ large subunit and a $Met^{1}$-[$Cys^{163}$ to $Ser^{163}$]-$His^{277}$ proenzyme. In the former case, the active site Cys residue in the large subunit (p17) is replaced with a Ser residue by site-directed mutagenesis. This large subunit is then re-folded with the recombinant p12 subunit to generate the mature form of the enzyme except with the active site Cys mutated to a Ser. In the latter case, the same $Cys^{163}$ to $Ser^{163}$ mutation is made, except that the entire proenzyme is expressed. In both cases, the resulting re-engineered polypeptides can be used in a binding assay by tethering the mutated enzymes to SPA beads via specific antibodies that are generated to recognize apopain (antibodies against the prodomain, the large p17 subunit, the small p12 subunit and the entire p17:p12 active enzyme have been generated). Epitope tags or GST and other fusions could also be used for this purpose and binding assay formats other than SPA can also be used. Ligands based on the prefered substrate for apopain (varients of AspGluValAsp), such as Ac-AspGluValAsp, Ac-AspGluValAsp-aldehydes, Ac-AspGluValAsp-ketones are suitable in their radiolabeled forms for SPA-based binding assays. Similar binding assays can also be established for other capsase family members.

DESCRIPTION OF THE SEQUENCE LISTINGS

SEQ ID NO. 1 is the top sense DNA strand of FIGS. 2A and 2B for the PTP1B tyrosine phosphatase enzyme.

SEQ ID NO. 2 is the amino acid sequence of FIGS. 2A and 2B for the PTP1B tyrosine phosphatase enzyme.

SEQ ID NO. 3 is the top sense cDNA strand of FIGS. 3A, 3B and 3C for the Cathepsin K preproenzyme.

SEQ ID NO. 4 is the amino acid sequence of FIGS. 3A, 3B and 3C for the Cathepsin K preproenzyme.

SEQ ID NO. 5 is the top sense cDNA strand of FIGS. 4A and 4B for the CPP32 apopain proenzyme.

SEQ ID NO. 6 is the amino acid sequence of FIGS. 4A and 4B for the CPP32 apopain proenzyme.

SEQ ID NO. 7 is the cDNA sequence of the human PTP-$1B_{1-320}$ Ser mutant.

SEQ ID NO. 8 is the amino acid sequence of the human PTP-$1B_{1-320}$ Ser mutant.

SEQ ID NO. 9 is the cDNA sequence for apopain C163S mutant.

SEQ ID NO. 10 is the amino acid sequence for the apopain C163S mutant.

SEQ ID NO. 11 is the large subunit of the heterodimeric amino acid sequence for the apopain C163S mutant.

SEQ ID NO. 12 is the cDNA sequence for the Cathepsin K C139S mutant.

SEQ ID NO. 13 is the cDNA sequence for the Cathepsin K C139A mutant.

SEQ ID NO. 14 is the amino acid sequence for the Cathepsin K C139S mutant.

SEQ ID NO. 15 is the amino acid sequence for the Cathepsin K C139A mutant.

```
                            SEQ ID NO. 1

ATGGAGATGGAAAAGGAGTTCGAGCAGATCGACAAGTCCGGGAGCTGGGCGGCCATTTAC
    1 ---------+---------+---------+---------+---------+---------+  60

CAGGATATCCGACATCAAGCCAGTCACTTCCCATCTAGAGTGGCCAAGCTTCCTAAGAAC
   61 ---------+---------+---------+---------+---------+---------+ 120

AAAAACCGAAATAGGTACAGAGACGTCAGTCCCTTTGACCATAGTCGGATTAAACTACAT
  121 ---------+---------+---------+---------+---------+---------+ 180

CAAGAAGATAATCACTATATCAACGCTAGTrTCATAAAAATGGAAGAAGCCCAAAGGAGT
  181 ---------+---------+---------+---------+---------+---------+ 240

TACATTCTTACCCAGGGCCCTTTGCCTAACACATCCGGTCACTTTTGGGAGATGGTCTGG
  241 ---------+---------+---------+---------+---------+---------+ 300

GAGCAGAAAAGCACGCGTCTCGTCATCCTCAACAGAGTCATGGAGAAAGGTTCGTTAAAA
  301 ---------+---------+---------+---------+---------+---------+ 360

TGCGCACAATACTGGCCACAAAAAGAAGAAAAAGAGATGATCTTTGAAGACACAAATTTG
  361 ---------+---------+---------+---------+---------+---------+ 420

AAATTAACATTGATCTCTCAAGATATCAAGTCATATTATACAGTGCGACAGCTAGAATTG
  421 ---------+---------+---------+---------+---------+---------+ 480
```

-continued

SEQ ID NO. 1

```
      GAAAACCTTACAACCCAAGAAACTCGAGAGATCTTACATTTCCACTATACCACATCGCCT
481   ---------+---------+---------+---------+---------+---------+ 540

GACTTTCGAGTCCCTGAATCACCAGCCTCATTCTTGAACTTTCTTTTCAAAGTCCGAGAG
541   ---------+---------+---------+---------+---------+---------+ 600

TCACGGTCACTCAGCCCGGAGCACGGGCCCGTTGTGGTGCACTGCAGTGCAGGCATCGGC
601   ---------+---------+---------+---------+---------+---------+ 660

AGGTCTGGAACCTTCTGTCTGGCTGATACCTGCCTCCTGCTGATGGACAAGAGGAAAGAC
661   ---------+---------+---------+---------+---------+---------+ 720

CCTTCTTCCGTTGATATCAAGAAAGTGCTGTTAGAAATGAGGAAGTTTCGGATGGGGTTG
721   ---------+---------+---------+---------+---------+---------+ 780

ATCCAGACAGCCGACCAGCTGCGCTTCTCCTACCTGGCTGTGATCGAAGGTGCCAAATTC
781   ---------+---------+---------+---------+---------+---------+ 840

ATCATGGGGGACTCTTCCGTGCAGGATCAGTGGAAGGAGCTTTGCCACGAGGACCTGGAG
841   ---------+---------+---------+---------+---------+---------+ 900

CCCCCACCCGAGCATATCCCCCCACCTCCCCGGCCACCCAAACGAATCCTGGAGCCACACTGA
901   ---------+---------+---------+---------+---------+---------+--- 960
```

SEQ ID NO. 2

```
  1 MetGluMetGluLysGluPheGluGlnIleAspLysSerGlySerTrpAlaAlaIleTyr  20
 21 GlnAspIleArgHisGluAlaSerAspPheProCysArgValAlaLysLeuProLysAsn  40
 41 LysAsnArgAsnArgTyrArgAspValSerProPheAspHisSerArgIleLysLeuHis  60
 61 GlnGluAspAsnAspTyrIleAsnAlaSerLeuIleLysMetGluGluAlaGlnArgSer  80
 81 TyrIleLeuThrGlnGlyProLeuProAsnThrCysGlyHisPheTrpGluMetValTrp 100
101 GluGlnLysSerArgGlyValValMetLeuAsnArgValMetGluLysGlySerLeuLys 120
121 CysAlaGlnTyrTrpProGlnLysGluGluLysGluMetIlePheGluAspThrAsnLeu 140
141 LysLeuThrLeuIleSerGluAspIleLysSerTyrTyrThrValArgGlnLeuGluLeu 160
161 GluAsnLeuThrThrGlnGluThrArgGluIleLeuHisPheHisTyrThrThrTrpPro 180
181 AspPheGlyValProGluSerProAlaSerPheLeuAsnPheLeuPheLysValArgGlu 200
201 SerGlySerLeuSerProGluHisGlyProValValValHis<u>Cys</u>SerAlaGlyIleGly 220
221 ArgSerGlyThrPheCysLeuAlaAspThrCysLeuLeuLeuMetAspLysArgLysAsp 240
241 ProSerSerValAspIleLysLysValLeuLeuGluMetArgLysPheArgMetGlyLeu 260
261 IleGlnThrAlaAspGlnLeuArgPheSerTyrLeuAlaValIleGluGlyAlaLysPhe 280
281 IleMetGlyAspSerSerValGlnAspGlnTrpLysGluLeuSerHisGluAspLeuGlu 300
301 ProProProGluHisIleProProProProArgProProLysArgIleLeuGluProHisEnd 320
```

SEQ ID NO. 3

```
    GAAACAAGCACTGGATTCCATATCCCACTGCCAAAACCGCATGGTTCAGATTATCGCTAT
1   ---------+---------+---------+---------+---------+---------+  60
    TGCAGCTTTCATCATAATACACACCTTTGCTGCCGAAACGAAGCCAGACAACAGATTTCC
```

SEQ ID NO. 3

```
 61 ---------+---------+---------+---------+---------+---------+  120
    ATCAGCAGGATGTGGGGGCTCAAGGTTCTGCTGCTACCTGTGGTGAGCTTTGCTCTGTAC
121 ---------+---------+---------+---------+---------+---------+  180
    CCTGAGGAGATACTGGACACCCACTGGGAGCTATGGAAGAAGACCCACAGGAAGCAATAT
181 ---------+---------+---------+---------+---------+---------+  240
    AACAACAAGGTGGATGAAATCTCTCGGCGTTTAATTTGGGAAAAAAACCTGAAGTATATT
241 ---------+---------+---------+---------+---------+---------+  300
    TCCATCCATAACCTTGAGGCTTCTCTTGGTGTCCATACATATGAACTGGCTATGAACCAC
301 ---------+---------+---------+---------+---------+---------+  360
    CTGGGGACATGACCAGTGAAGAGGTGGTTCAGAAGATGACTGGACTCAAAGTACCCCTG
361 ---------+---------+---------+---------+---------+---------+  420
    TCTCATTCCCGCAGTAATGACACCCTTTATATCCCAGAATGGGAAGGTAGAGCCCCAGAC
421 ---------+---------+---------+---------+---------+---------+  480
    TCTGTCGACTATCGAAAGAAAGGATATGTTACTCCTGTCAAAAATCAGGGTCAGTGTGGT
481 ---------+---------+---------+---------+---------+---------+  540
    TCCTGTTGGGCTTTTAGCTCTGTGGGTGCCCTGGAGGGCCAACTCAAGAAGAAAACTGGC
541 ---------+---------+---------+---------+---------+---------+  600
    AAACTCTTAAATCTGAGTCCCCAGAACCTAGTGGATTGTGTGTCTGAGAATGATGGCTGT
601 ---------+---------+---------+---------+---------+---------+  660
    GGAGGGGGCTACATGACCAATGCCTTCCAATATGTGCAGAAGAACCGGGGTATTGACTCT
661 ---------+---------+---------+---------+---------+---------+  720
    GAAGATGCCTACCCATATGTGGGACAGGAAGAGAGTTGTATGTACAACCCAACAGGCAAG
721 ---------+---------+---------+---------+---------+---------+  780
    GCAGCTAAATGCAGAGGGTACAGAGAGATCCCCGAGGGGAATGAGAAAGCCCTGAAGAGG
781 ---------+---------+---------+---------+---------+---------+  840
    GCAGTGGCCCGAGTGGGACCTGTCTCTGTGGCCATTGATGCAAGCCTGACCTCCTTCCAG
841 ---------+---------+---------+---------+---------+---------+  900
    TTTTACAGCAAAGGTGTGTATTATGATGAAAGCTGCAATAGCGATAATCTGAACCATGCG
901 ---------+---------+---------+---------+---------+---------+  960
    GTTTTGGCAGTGGGATATGGAATCCAGAAGGGAAACAAGCACTGGATAATTAAAAACAGC
961 ---------+---------+---------+---------+---------+---------+ 1020
    TGGGGAGAAAACTGGGGAAACAAAGGATATATCCTCATGGCTCGAAATAAGAACAACGCC
1021 ---------+---------+---------+---------+---------+---------+ 1080
    TGTGGCATTGCCAACCTGGCCAGCTTCCCCAAGATGTGACTCCAGCCAGCCAAATCCATC
1081 ---------+---------+---------+---------+---------+---------+ 1140
    CTGCTCTTCCATTTCTTCCACGATGGTGCAGTGTAACGATGCACTTTGGAAGGGAGTTGG
1141 ---------+---------+---------+---------+---------+---------+ 1200
    TGTGCTATTTTTGAAGCAGATGTGGTGATACTGAGATTGTCTGTTCAGTTTCCCCATTTG
1201 ---------+---------+---------+---------+---------+---------+ 1260
    TTTGTGCTTCAAATGATCCTTCCTACTTTGCTTCTCTCCACCCATGACCTTTTTCACTGT
1261 ---------+---------+---------+---------+---------+---------+ 1320
    GGCCATCAGGACTTTCCCTGACAGCTGTGTACTCTTAGGCTAAGAGATGTGACTACAGCC
1321 ---------+---------+---------+---------+---------+---------+ 1380
```

SEQ ID NO. 3

```
     TGCCCCTGACTGTGTTGTCCCAGGGCTGATGCTGTACAGGTACAGGCTGGAGATTTTCAC
1381 ---------+---------+---------+---------+---------+---------+ 1440

ATAGGTTAGATTCTCATTCACGGGACTAGTTAGCTTTAAGCACCCTAGAGGACTAGGGTA
1441 ---------+---------+---------+---------+---------+---------+ 1500

ATCTGACTTCTCACTTCCTAAGTTCCCTTCTATATCCTCAAGGTAGAAATGTCTATGTTT
1501 ---------+---------+---------+---------+---------+---------+ 1560

TCTACTCCAATTCATAAATCTATTCATAAGTCTTTGGTACAAGTTTACATGATAAAAGA
1561 ---------+---------+---------+---------+---------+---------+ 1620

AATGTGATTTGTCTTCCCTTCTTTGCACTTTTGAAATAAAGTATTTATC
1621 ---------+---------+---------+---------+--------- 1669
```

SEQ ID NO. 4

MetTrpGlyLeuLysValLeuLeuLeuProValValSerPheAlaLeuTyr

ProGluGluIleLeuAspThrHisTrpGluLeuTrpLysLysThrHisArgLysGlnTyr

AsnAsnLysValAspGluIleSerArgArgLeuIleTrpGluLysAsnLeuLysTyrIle

SerIleHisAsnLeuGluAlaSerLeuGlyValHisThrTyrGluLeuAlaMetAsnHis

LeuGlyAspMetThrSerGluGluValValGlnLysMetThrGlyLeuLysValProLeu

SerHisSerArgSerAsnAspThrLeuTyrIleProGluTrpGluGlyArgAlaProAsp

SerValAspTyrArgLysLysGlyTyrValThrProValLysAsnGlnGlyGlnCysGly

SerCysTrpAlaPheSerSerValGlyAlaLeuGluGlyGlnLeuLysLysLysThrGly
   139

LysLeuLeuAsnLeuSerProGlnAsnLeuValAspCysValSerGluAsnAspGlyCys

GlyGlyGlyTyrMetThrAsnAlaPheGlnTyrValGlnLysAsnArgGlyIleAspSer

GluAspAlaTyrProTyrValGlyGlnGluGluSerCysMetTyrAsnProThrGlyLys

AlaAlaLysCysArgGlyTyrArgGluIleProGluGlyAsnGluLysAlaLeuLysArg

AlaValAlaArgValGlyProValSerValAlaIleAspAlaSerLeuThrSerPheGln

PheTyrSerLysGlyValTyrTyrAspGluSerCysAsnSerAspAsnLeuAsnHisAla

ValLeuAlaValGlyTyrGlyIleGlnLysGlyAsnLysHisTrpIleIleLysAsnSer

TrpGlyGluAsnTrpGlyAsnLysGlyTyrIleLeuMetAlaArgAsnLysAsnAsnAla

CysGlyIleAlaAsnLeuAlaSerPheProLysMetEnd

SEQ ID NO. 5

```
   CTGCAGGAATTCGGCACGAGGGGTGCTATTGTGAGGCGGTTGTAGAAGTTAATAAAGGTA
 1 ---------+---------+---------+---------+---------+---------+ 60

TCCATGGAGAACACTGAAAACTCAGTGGATTCAAAATCCATTAAAAATTTGGAACCAAAG
61 ---------+---------+---------+---------+---------+---------+ 120

ATCATACATGGAAGCGAATCAATGGACTCTGGAATATCCCTGGACAACAGTTATAAAATG
121 ---------+---------+---------+---------+---------+---------+ 180

GATTATCCTGAGATGGGTTTATGTATAATAATTAATAATAAGAATTTTCATAAGAGCACT
```

SEQ ID NO. 5

```
181 ---------+---------+---------+---------+---------+---------+ 240
    GGAATGACATCTCGGTCTGGTACAGATGTCGATGCAGCAAACCTCAGGGAAACATTCAGA
241 ---------+---------+---------+---------+---------+---------+ 300
    AACTTGAAATATGAAGTCAGGAATAAAAATGATCTTACACGTGAAGAAATTGTGGAATTG
301 ---------+---------+---------+---------+---------+---------+ 360
    ATGCGTGATGTTTCTAAAGAAGATCACAGCAAAAGGAGCAGTTTTGTTTGTGTGCTTCTG
361 ---------+---------+---------+---------+---------+---------+ 420
    AGCCATGGTGAAGAAGGAATAATTTTTGGAACAAATGGACCTGTTGACCTGAAAAAAATA
421 ---------+---------+---------+---------+---------+---------+ 480
    ACAAACTTTTTCAGAGGGGATCGTTGTAGAAGTCTAACTGGAAAACCCAAACTTTTCATT
481 ---------+---------+---------+---------+---------+---------+ 540
    ATTCAGGCCTGCCGTGGTACAGAACTGGACTGTGGCATTGAGACAGACAGTGGTGTTGAT
541 ---------+---------+---------+---------+---------+---------+ 600
    GATGACATGGCGTGTCATAAAATACCAGTGGAGGCCGACTTCTTGTATGCATACTCCACA
601 ---------+---------+---------+ ---------+---------+---------+ 660
    GCACCTGGTTATTATTCTTGGCGAAATTCAAAGGATGGCTCCTGGTTCATCCAGTCGCTT
661 ---------+---------+---------+---------+---------+---------+ 720
    TGTGCCATGCTGAAACAGTATGCCGACAAGCTTGAATTTATGCACATTCTTACCCGGGTT
721 ---------+---------+---------+---------+---------+---------+ 780
    AACCGAAAGGTGGCAACAGAATTTGAGTCCTTTTCCTTTGACGCTACTTTTCATGCAAAG
781 ---------+---------+---------+---------+---------+---------+ 840
    AAACAGATTCCATGTATTGTTTCCATGCTCACAAAAGAACTCTATTTTTATCACTAAAGA
841 ---------+---------+---------+---------+---------+---------+ 900
    AATGGTTGGTTGGTGGTTTTTTTTAGTTTGTATGCCAAGTGAGAAGATGGTATATTTGGT
901 ---------+---------+---------+---------+---------+---------+ 960
    ACTGTATTTCCCTCTCATTTTGACCTACTCTCATGCTGCAG
961 ---------+---------+---------+---------+- 1001
```

SEQ ID NO. 6

MetGluAsnThrGluAsnSerValAspSerLysSerIleLysAsnLeuGluProLys

IleIleHisGlySerGluSerMetAspSerGlyIleSerLeuAspAsnSerTyrLysMet

AspTyrProGluMetGlyLeuCysIleIleIleAsnAsnLysAsnPheHisLysSerThr

GlyMetThrSerArgSerGlyThrAspValAspAlaAlaAsnLeuArgGluThrPheArg

AsnLeuLysTyrGluValArgAsnLysAsnAspLeuThrArgGluGluIleValGluLeu

MetArgAspValSerLysGluAspHisSerLysArgSerSerPheValCysValLeuLeu

SerHisGlyGluGluGlyIleIlePheGlyThrAsnGlyProValAspLeuLysLysIle

ThrAsnPhePheArgGlyAspArgCysArgSerLeuThrGlyLysProLysLeuPheIle

IleGlnAla<u>Cys</u>ArgGlyThrGluLeuAspCysGlyIleGluThrAspSerGlyValAsp
      163

AspAspMetAlaCysHisLysIleProValGluAlaAspPheLeuTyrAlaTyrSerThr

AlaProGlyTyrTyrSerTrpArgAsnSerLysAspGlySerTrpPheIleGlnSerLeu

SEQ ID NO. 6

CysAlaMetLeuLysGlnTyrAlaAspLysLeuGluPheMetHisIleLeuThrArgVal

AsnArgLysValAlaThrGluPheGluSerPheSerPheAspAlaThrPheHisAlaLys

LysGlnIleProCysIleValSerMetLeuThrLysGluLeuTyrPheTyrHisEnd

SEQ ID NO. 7

```
ATGGAGATGGAAAAGGAGTTCGAGCAGATCGACAAGTCCGGGAGCTGGGCG
GCCATTTAC
    1   --------+---------+---------+---------+--
------+---------+   60

CAGGATATCCGACATGAAGCCAGTGACTTCCCATGTAGAGTGGCCAAGCTT
CCTAAGAAC
   61   --------+---------+---------+---------+--
------+---------+  120

AAAAACCGAAATAGGTACAGAGACGTCAGTCCCTTTGACCATAGTCGGATT
AAACTACAT
  121   --------+---------+---------+---------+--
------+---------+  180

CAAGAAGATAATGACTATATCAACGCTAGTTTGATAAAAATGGAAGAAGCC
CAAAGGAGT
  181   --------+---------+---------+---------+--
------+---------+  240

TACATTCTTACCCAGGGCCCTTTGCCTAACACATGCGGTCACTTTTGGGAG
ATGGTGTGG
  241   --------+---------+---------+---------+--
------+---------+  300

GAGCAGAAAAGCAGGGGTGTCGTCATGCTCAACAGAGTGATGGAGAAAGGT
TCGTTAAAA
  301   --------+---------+---------+---------+--
------+---------+  360

TGCGCACAATACTGGCCACAAAAAGAAGAAAAAGAGATGATCTTTGAAGAC
ACAAATTTG
  361   --------+---------+---------+---------+--
------+---------+  420

AAATTAACATTGATCTCTGAAGATATCAAGTCATATTATACAGTGCGACAG
CTAGAATTG
  421   --------+---------+---------+---------+--
------+---------+  480

GAAAACCTTACAACCCAAGAAACTCGAGAGATCTTACATTTCCACTATACC
ACATGGCCT
  481   --------+---------+---------+---------+--
------+---------+  540

GACTTTGGAGTCCCTGAATCACCAGCCTCATTCTTGAACTTTCTTTTCAAA
GTCCGAGAG
  541   --------+---------+---------+---------+--
------+---------+  600

TCAGGGTCACTCAGCCCGGAGCACGGGCCGTTGTGGTGCACTGCAGTGCA
GGCATCGGC
  601   --------+---------+---------+---------+--
------+---------+  660

AGGTCTGGAACCTTCTGTCTGGCTGATACCTGCCTCCTGCTGATGGACAAG
AGGAAAGAC
  661   --------+---------+---------+---------+--
------+---------+  720

CCTTCTTCCGTTGATATCAAGAAAGTGCTGTTAGAAATGAGGAAGTTTCGG
ATGGGGTTG
  721   --------+---------+---------+---------+--
------+---------+  780

ATCCAGACAGCCGACCAGCTGCGCTTCTCCTACCTGGCTGTGATCGAAGGT
GCCAAATTC
  781   --------+---------+---------+---------+--
------+---------+  840

ATCATGGGGGACTCTTCCGTGCAGGATCAGTGGAAGGAGCTTTCCCACGAG
GACCTGGAG
  841   --------+---------+---------+---------+--
------+---------+  900

CCCCCACCCGAGCATATCCCCCCACCTCCCCGGCCACCCAAACGAATCCTG
GAGCCACACTGA
  901   --------+---------+---------+---------+--
------+---------+---  960
```

SEQ ID NO. 8

MetGluMetGluLysGluPheGluGlnIleAspLysSerGlySerTrpAla
AlaIleTyr    20

GlnAspIleArgHisGluAlaSerAspPheProCysArgValAlaLysLeu
ProLysAsn    40

LysAsnArgAsnArgTyrArgAspValSerProPheAspHisSerArgIle
LysLeuHis    60

GlnGluAspAsnAspTyrIleAsnAlaSerLeuIleLysMetGluGluAla
GlnArgSer    80

TyrIleLeuThrGlnGlyProLeuProAsnThrCysGlyHisPheTrpGlu
MetValTrp   100

GluGlnLysSerArgGlyValValMetLeuAsnArgValMetGluLysGly
SerLeuLys   120

CysAlaGlnTyrTrpProGlnLysGluGluLysGluMetIlePheGluAsp
ThrAsnLeu   140

LysLeuThrLeuIleSerGluAspIleLysSerTyrTyrThrvAlargGln
LeuGluLeu   160

GluAsnLeuThrThrGlnGluThrArgGluIleLeuHisPheHisTyrThr
ThrTrpPro   180

AspPheGlyValProGluSerProAlaSerPheLeuAsnPheLeuPheLys
ValArgGlu   200

SEQ ID NO. 8

SerGlySerLeuSerProGluHisGlyProValValValHisCysSerAla
GlyIleGly   220
{TCG}

ArgSerGlyThrPheCysLeuAlaAspThrCysLeuLeuLeuMetAspLys
ArgLysAsp   240

ProSerSerValAspIleLysLysValLeuLeuGluMetArgLysPheArg
MetGlyLeu   260

IleGlnThrAlaAspGlnLeuArgPheSerTyrLeuAlaValIleGluGly
AlaLysPhe   280

IleMetGlyAspSerSerValGlnAspGlnTrpLysGluLeuSerHisGlu
AspLeuGlu   300

ProProProGluHisIleProProProProArgProProLysArgIleLeu
GluProHisEnd   320

SEQ ID NO. 9

```
   1 CTGCAGGAAT TCGGCACGAG GGGTGCTATT GTGAGGCGGT TGTAGAAGTT
  51 AATAAAGGTA TCCATGGAGA ACACTGAAAA CTCAGTGGAT TCAAAATCCA
 101 TTAAAAATTT GGAACCAAAG ATCATACATG GAAGCGAATC AATGGACTCT
 151 GGAATATCCC TGGACAACAG TTATAAAATG GATTATCCTG AGATGGGTTT
 201 ATGTATAATA ATTAATAATA AGAATTTTCA TAAGAGCACT GGAATGACAT
 251 CTCGGTCTGG TACAGATGTC GATGCAGCAA ACCTCAGGGA ACATTCAGA
 301 AACTTGAAAT ATGAAGTCAG GAATAAAAAT GATCTTACAC GTGAAGAAAT
 351 TGTGGAATTG ATGCGTGATG TTTCTAAAGA AGATCACAGC AAAAGGAGCA
 401 GTTTTGTTTG TGTGCTTCTG AGCCATGGTG AAGAAGGAAT AATTTTTGGA
 451 ACAAATGGAC CTGTTGACCT GAAAAAAATA ACAAACTTTT TCAGAGGGGA
 501 TCGTTGTAGA AGTCTAACTG AAAACCCAA ACTTTTCATT ATTCAGGCC<u>T</u>
 551 <u>CCC</u>GTGGTAC AGAACTGGAC TGTGGCATTG AGACAGACAG TGGTGTTGAT
 601 GATGACATGG CGTGTCATAA AATACCAGTG GAGGCCGACT TCTTGTATGC
 651 ATACTCCACA GCACCTGGTT ATTATTCTTG GCGAAATTCA AAGGATGGCT
 701 CCTGGTTCAT CCAGTCGCTT TGTGCCATGC TGAAACAGTA TGCCGACAAG
 751 CTTGAATTTA TGCACATTCT TACCCGGGTT AACCGAAAGG TGGCAACAGA
 801 ATTTGAGTCC TTTTCCTTTG ACGCTACTTT TCATGCAAAG AAACAGATTC
 851 CATGTATTGT TTCCATGCTC ACAAAAGAAC TCTATTTTTA TCACTAAAGA
 901 AATGGTTGGT TGGTGGTTTT TTTTAGTTTG TATGCCAAGT GAGAAGATGG
 951 TATATTTGGT ACTGTATTTC CCTCTCATTT TGACCTACTC TCATGCTGCA
1001 G
```

| SEQ ID NO. 10 |
|---|
| 1 MENTENSVDS KSIKNLEPKI IHGSESMDSG ISLDNSYKMD YPEMGLCIII |
| 51 NKKNFHKSTG MTSRSGTDVD AANLRETFRN LKYEVDNKND LTREEIVELM |
| 101 RDVSKEDHSK RSSFVCVLLS HGEEGIIFGT NGPVDLKKIT NFFRGDRCRS |
| 151 LTGKPKLFII QA<u>S</u>RGTELDC GIETDSGVDD DMACHKIPVE ADFLYAYSTA |
| 201 PGYYSWRNSK DGSWFIQSLC AMLKQYADKL EFMHILTRVN RKVATEFESF |
| 251 SFDATFHAKK QIPCIVSMLT KELYFYH |

| SEQ ID NO. 11 |
|---|
| 1 MSG ISLDNSYKMD YPEMGLCIII |
| 51 NNKNFHKSTG MTSRSGTDVD AANLRETFRN LKYEVRNKND LTREEIVELM |
| 101 RDVSKEDHSK RSSFVCVLLS HGEEGIIFGT NGPVDLKKIT NFFRGDRCRS |
| 151 LTGKPKLFII QA<u>S</u>RGTELDC GIETD |

| SEQ ID NO. 12 |
|---|
| 1 ATGTGGGGC TCAAGGTTCT GCTGCTACCT GTGGTGAGCT TGCTCTGTA |
| 51 CCCTGAGGAG ATACTGGACA CCCACTGGGA GCTATGGAAG AAGACCCACA |
| 101 GGAAGCAATA TAACAACAAG GTGGATGAAA TCTCTCGGCG TTTAATTTGG |
| 151 GAAAAAAACC TGAAGTATAT TTCCATCCAT AACCTTGAGG CTTCTCTTGG |
| 201 TGTCCATACA TATGAACTGG CTATGAACCA CCTCGGGGAC ATGACCAGTG |
| 251 AAGAGGTGGT TCAGAAGATG ACTGGACTCA AGTACCCCT GTCTCATTCC |
| 301 CGCAGTAATG ACACCCTTTA TATCCCAGAA TGGGAAGGTA GAGCCCCAGA |
| 351 CTCTGTCGAC TATCGAAAGA AGGATATGT TACTCCTGTC AAAAATCAGG |
| 401 GTCAGTGTGG TTCC<u>TCT</u>TGG GCTTTTAGCT CTGTGGGTGC CCTGGAGGGC |
| 451 CAACTCAAGA AGAAAACTGG CAAACTCTTA AATCTGAGTC CCAGAACCT |
| 501 AGTGGATTGT GTGTCTGAGA ATGATGGCTG TGGAGGGGGC TACATGACCA |
| 551 ATGCCTTCCA ATATGTGCAG AAGAACCGGG GTATTGACTC TGAAGATGCC |
| 601 TACCCATATG TGGGACAGGA AGAGAGTTGT ATGTACAACC CAACAGGCAA |
| 651 GGCAGCTAAA TGCAGAGGGT ACAGAGAGAT CCCCGAGGGG AATGAGAAAG |
| 701 CCCTGAAGAG GCAGTGGCC CGAGTGGGAC CTGTCTCTGT GGCCATTGAT |
| 751 GCAAGCCTGA CCTCCTTCCA GTTTTACAGC AAAGGTGTGT ATTATGATGA |
| 801 AAGCTGCAAT AGCGATAATC TGAACCATGC GGTTTTGGCA GTGGGATATG |
| 851 GAATCCAGAA GGGAAACAAG CACTGGATAA TTAAAAACAG CTGGGGAGAA |
| 901 AACTGGGGAA ACAAGGATA TATCCTCATG GCTCGAAATA GAACAACGC |
| 951 CTGTGGCATT GCCAACCTGG CCAGCTTCCC CAAGATGTGA |

| SEQ ID NO. 13 |
|---|
| 1 ATGTGGGGC TCAAGGTTCT GCTGCTACCT GTGGTGAGCT TTGCTCTGTA |
| 51 CCCTGAGGAG ATACTGGACA CCCACTGGGA GCTATGGAAG AAGACCCACA |
| 101 GGAAGCAATA TAACAACAAG GTGGATGAAA TCTCTCGGCG TTTAATTTGG |
| 151 GAAAAAAACC TGAAGTATAT TTCCATCCAT AACCTTGAGG CTTCTCTTGG |
| 201 TGTCCATACA TATGAACTGG CTATGAACCA CCTGCGGGAC ATGACCAGTG |
| 251 AAGAGGTGGT TCAGAAGATG ACTGGACTCA AGTACCCCT GTCTCATTCC |
| 301 CGCAGTAATG ACACCCTTTA TATCCCAGAA TGGGAAGGTA GAGCCCCAGA |
| 351 CTCTGTCGAC TATCGAAAGA AGGATATGT TACTCCTGTC AAAAATCAGG |
| 401 GTCAGTGTGG TTCCGCTTGG GCTTTTAGCT CTGTGGGTGC CCTGGAGGGC |
| 451 CAACTCAAGA AGAAAACTGG CAAACTCTTA AATCTGAGTC CCCAGAACCT |
| 501 AGTGGATTGT GTGTCTGAGA ATGATGGCTG TGGAGGGGGC TACATGACCA |
| 551 ATGCCTTCCA ATATGTGCAG AAGAACCGGG GTATTGACTC TGAAGATGCC |
| 601 TACCCATATG TGGGACAGGA AGAGAGTTGT ATGTACAACC CAACAGGCAA |
| 651 GGCAGCTAAA TGCAGAGGGT ACAGAGAGAT CCCCGAGGGG AATGAGAAAG |
| 701 CCCTGAAGAG GGCAGTGGCC CGAGTGGGAC TGTCTCTGT GGCCATTGAT |
| 751 GCAAGCCTGA CCTCCTTCCA GTTTTACAGC AAAGGTGTGT ATTATGATGA |
| 801 AAGCTGCAAT AGCGATAATC TGAACCATGC GGTTTTGGCA GTGGGATATG |
| 851 GAATCCAGAA GGGAAACAAG CACTGGATAA TTAAAAACAG CTGGGGAGAA |
| 901 AACTGGGGAA ACAAAGGATA TATCCTCATG GCTCGAAATA AGAACAACGC |
| 951 CTGTGGCATT GCCAACCTGG CCAGCTTCCC CAAGATGTGA |

| SEQ ID NO. 14 |
|---|
| 1 MWGLKVLLLP VVSFALYPEE ILDTHWELWK KTHRKQYNNK VDEISRRLIW |
| 51 EKNLKYISIH NLEASLGVHT YELAMNHLGD MTSEEVVQKM TGLKVPLSHS |
| 101 RSNDTLYIPE WEGRAPDSVD YRKKGYVTPV KNQGQCGSSW AFSSVGALEG |
| 151 QLKKKTGKLL NLSPQNLVDC VSENDCGGG YMTNAFQYVQ KNRGIDSEDA |
| 201 YPYVGQEESC MYNPTGKAAK CRGYREIPEG NEKALKRAVA RVGPVSVAID |
| 251 ASLTSFQFYS KGVYYDESCN SDNLNHAVLA VGYGIQKGNK HWIIKNSWGE |
| 301 NWGNKGYILM ARNKNNACGI ANLASFPKM |

| SEQ ID NO. 15 |
|---|
| 1 MWGLKVLLLP VVSFALYPEE ILDTHWELWK KTHRKQYNNK VDEISRRLIW |
| 51 EKNLKYISIH NLEASLGVHT YELAMNHLGD MTSEEVVQKM TGLKVPLSHS |
| 101 RSNDTLYIPE WEGRAPDSVD YRKKGYVTPV KNQGQCGS<u>A</u>W AFSSVGALEG |
| 151 QLKKKTGKLL NLSPQNLVDC VSENDGCGGG YMTNAFQYVQ KNRGIDSEDA |
| 201 YPYVGQEESC MYNPTGKAAK CRGYREIPEG NEKALKRAVA RVGPVSVAID |
| 251 ASLTSFQFYS KGVYYDESCN SDNLNHAVLA VGYGIQKGNK HWIIKNSWGE |
| 301 NWGNKGYILM ARNKNNACGI ANLASFPKM |

What is claimed:

1. A tripeptide that contains two 4-phosphono (difluoromethyl)phenylalanine groups.

2. The tripeptide of claim 1 selected from the group consisting of:
- N-Benzoyl-L-glutamyl-(4-phosphono(difluoromethyl))-L-phenylalanyl-(4-phosphono(difluoromethyl))-L-phenylalanine amide;
- N-(3,5-Dibromo-benzoyl)-L-glutamyl-(4-phosphono(difluoromethyl))-L-phenylalanyl-(4-phosphono(difluoromethyl))-L-phenylalanine amide;
- N-Acetyl-L-glutamyl-(4-phosphono(difluoromethyl))-L-phenylalanyl-(4-phosphono(difluoromethyl))-L-phenylalanine amide;
- L-Glutamyl-(4-phosphono(difluoromethyl))-L-phenylalanyl-(4-phosphono(difluoromethyl))-L-phenylalanine amide;
- L-Lysinyl-(4-phosphono(difluoromethyl))-L-phenylalanyl-(4-phosphono(difluoromethyl))-L-phenylalanine amide;

L-Serinyl-(4-phosphono(difluoromethyl))-L-phenylalanyl-(4-phosphono(difluoromethyl))-L-phenylalanine amide;

L-Prolinyl-(4-phosphono(difluoromethyl))-L-phenylalanyl-(4-phosphono(difluoromethyl))-L-phenylalanine amide;

L-Isoleucinyl-(4-phosphono(difluoromethyl))-L-phenylalanyl-(4-phosphono(difluoromethyl))-L-phenylalanine amide.

3. The tripeptide of claim 1 in tritiated or $I^{125}$-iodinated form.

4. The tritiated tripeptide of claim 3:

N-(3,5-Ditritio)-benzoyl-L-glutamyl-(4-phosphono(difluoromethyl))-L-phenylalanyl-(4-phosphono(difluoromethyl))-L-phenylalanine amide.

* * * * *

SEQUENCE LISTING (1) GENERAL INFORMATION:

(iii) NUMBER OF SEQUENCES: 15

(2) INFORMATION FOR SEQ ID NO:1:

(i) SEQUENCE CHARACTERISTICS:
      (A) LENGTH: 963 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
ATGGAGATGG AAAAGGAGTT CGAGCAGATC GACAAGTCCG GGAGCTGGGC GGCCATTTAC      60
CAGGATATCC GACATGAAGC CAGTGACTTC CCATGTAGAG TGGCCAAGCT TCCTAAGAAC     120
AAAAACCGAA ATAGGTACAG AGACGTCAGT CCCTTTGACC ATAGTCGGAT TAAACTACAT     180
CAAGAAGATA ATGACTATAT CAACGCTAGT TTGATAAAAA TGGAAGAAGC CCAAAGGAGT     240
TACATTCTTA CCCAGGGCCC TTTGCCTAAC ACATGCGGTC ACTTTTGGGA GATGGTGTGG     300
GAGCAGAAAA GCAGGGGTGT CGTCATGCTC AACAGAGTGA TGGAGAAAGG TTCGTTAAAA     360
TGCGCACAAT ACTGGCCACA AAAAGAAGAA AAAGAGATGA TCTTTGAAGA CACAAATTTG     420
AAATTAACAT TGATCTCTGA AGATATCAAG TCATATTATA CAGTGCGACA GCTAGAATTG     480
GAAAACCTTA CAACCCAAGA AACTCGAGAG ATCTTACATT CCACTATAC CACATGGCCT     540
GACTTTGGAG TCCCTGAATC ACCAGCCTCA TTCTTGAACT TTCTTTTCAA AGTCCGAGAG     600
TCAGGGTCAC TCAGCCCGGA GCACGGGCCC GTTGTGGTGC ACTGCAGTGC AGGCATCGGC     660
AGGTCTGGAA CCTTCTGTCT GGCTGATACC TGCCTCCTGC TGATGGACAA GAGGAAAGAC     720
CCTTCTTCCG TTGATATCAA GAAAGTGCTG TTAGAAATGA GGAAGTTTCG GATGGGGTTG     780
ATCCAGACAG CCGACCAGCT GCGCTTCTCC TACCTGGCTG TGATCGAAGG TGCCAAATTC     840
ATCATGGGGG ACTCTTCCGT GCAGGATCAG TGGAAGGAGC TTTCCCACGA GGACCTGGAG     900
CCCCCACCCG AGCATATCCC CCCACCTCCC CGGCCACCCA AACGAATCCT GGAGCCACAC     960
TGA                                                                  963
```

(2) INFORMATION FOR SEQ ID NO:2:

(i) SEQUENCE CHARACTERISTICS:

(A) LENGTH: 320 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

Met Glu Met Glu Lys Glu Phe Glu Gln Ile Asp Lys Ser Gly Ser Trp
1               5                   10                  15

Ala Ala Ile Tyr Gln Asp Ile Arg His Glu Ala Ser Asp Phe Pro Cys
            20                  25                  30

Arg Val Ala Lys Leu Pro Lys Asn Lys Asn Arg Asn Arg Tyr Arg Asp
        35                  40                  45

Val Ser Pro Phe Asp His Ser Arg Ile Lys Leu His Gln Glu Asp Asn
    50                  55                  60

Asp Tyr Ile Asn Ala Ser Leu Ile Lys Met Glu Glu Ala Gln Arg Ser
65                  70                  75                  80

Tyr Ile Leu Thr Gln Gly Pro Leu Pro Asn Thr Cys Gly His Phe Trp
                85                  90                  95

Glu Met Val Trp Glu Gln Lys Ser Arg Gly Val Val Met Leu Asn Arg
            100                 105                 110

Val Met Glu Lys Gly Ser Leu Lys Cys Ala Gln Tyr Trp Pro Gln Lys
        115                 120                 125

Glu Glu Lys Glu Met Ile Phe Glu Asp Thr Asn Leu Lys Leu Thr Leu
    130                 135                 140

Ile Ser Glu Asp Ile Lys Ser Tyr Tyr Thr Val Arg Gln Leu Glu Leu
145                 150                 155                 160

Glu Asn Leu Thr Thr Gln Glu Thr Arg Glu Ile Leu His Phe His Tyr
                165                 170                 175

Thr Thr Trp Pro Asp Phe Gly Val Pro Glu Ser Pro Ala Ser Phe Leu
            180                 185                 190

Asn Phe Leu Phe Lys Val Arg Glu Ser Gly Ser Leu Ser Pro Glu His
        195                 200                 205

Gly Pro Val Val Val His Cys Ser Ala Gly Ile Gly Arg Ser Gly Thr
    210                 215                 220

Phe Cys Leu Ala Asp Thr Cys Leu Leu Leu Met Asp Lys Arg Lys Asp
225                 230                 235                 240

Pro Ser Ser Val Asp Ile Lys Lys Val Leu Leu Glu Met Arg Lys Phe
                245                 250                 255

Arg Met Gly Leu Ile Gln Thr Ala Asp Gln Leu Arg Phe Ser Tyr Leu
            260                 265                 270

Ala Val Ile Glu Gly Ala Lys Phe Ile Met Gly Asp Ser Ser Val Gln
        275                 280                 285

Asp Gln Trp Lys Glu Leu Ser His Glu Asp Leu Glu Pro Pro Pro Glu
    290                 295                 300

His Ile Pro Pro Pro Arg Pro Pro Lys Arg Ile Leu Glu Pro His
305                 310                 315                 320

(2) INFORMATION FOR SEQ ID NO:3:

(i) SEQUENCE CHARACTERISTICS:
        (A) LENGTH: 1669 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

```
GAAACAAGCA CTGGATTCCA TATCCCACTG CCAAAACCGC ATGGTTCAGA TTATCGCTAT     60
TGCAGCTTTC ATCATAATAC ACACCTTTGC TGCCGAAACG AAGCCAGACA ACAGATTTCC    120
ATCAGCAGGA TGTGGGGGCT CAAGGTTCTG CTGCTACCTG TGGTGAGCTT TGCTCTGTAC    180
CCTGAGGAGA TACTGGACAC CCACTGGGAG CTATGGAAGA AGACCCACAG GAAGCAATAT    240
AACAACAAGG TGGATGAAAT CTCTCGGCGT TTAATTTGGG AAAAAAACCT GAAGTATATT    300
TCCATCCATA ACCTTGAGGC TTCTCTTGGT GTCCATACAT ATGAACTGGC TATGAACCAC    360
CTGGGGACA TGACCAGTGA AGAGGTGGTT CAGAAGATGA CTGGACTCAA AGTACCCCTG     420
TCTCATTCCC GCAGTAATGA CACCCTTTAT ATCCCAGAAT GGGAAGGTAG AGCCCCAGAC    480
TCTGTCGACT ATCGAAAGAA AGGATATGTT ACTCCTGTCA AAAATCAGGG TCAGTGTGGT    540
TCCTGTTGGG CTTTTAGCTC TGTGGGTGCC CTGGAGGGCC AACTCAAGAA GAAAACTGGC    600
AAACTCTTAA ATCTGAGTCC CCAGAACCTA GTGGATTGTG TGTCTGAGAA TGATGGCTGT    660
GGAGGGGGCT ACATGACCAA TGCCTTCCAA TATGTGCAGA AGAACCGGGG TATTGACTCT    720
GAAGATGCCT ACCCATATGT GGGACAGGAA GAGAGTTGTA TGTACAACCC AACAGGCAAG    780
GCAGCTAAAT GCAGAGGGTA CAGAGAGATC CCCGAGGGGA ATGAGAAAGC CCTGAAGAGG    840
GCAGTGGCCC GAGTGGGACC TGTCTCTGTG GCCATTGATG CAAGCCTGAC CTCCTTCCAG    900
TTTTACAGCA AAGGTGTGTA TTATGATGAA AGCTGCAATA GCGATAATCT GAACCATGCG    960
GTTTTGGCAG TGGGATATGG AATCCAGAAG GGAAACAAGC ACTGGATAAT TAAAAACAGC   1020
TGGGGAGAAA ACTGGGGAAA CAAAGGATAT ATCCTCATGG CTCGAAATAA GAACAACGCC   1080
TGTGGCATTG CCAACCTGGC CAGCTTCCCC AAGATGTGAC TCCAGCCAGC CAAATCCATC   1140
CTGCTCTTCC ATTTCTTCCA CGATGGTGCA GTGTAACGAT GCACTTTGGA AGGGAGTTGG   1200
TGTGCTATTT TTGAAGCAGA TGTGGTGATA CTGAGATTGT CTGTTCAGTT TCCCCATTTG   1260
TTTGTGCTTC AAATGATCCT TCCTACTTTG CTTCTCTCCA CCCATGACCT TTTTCACTGT   1320
GGCCATCAGG ACTTTCCCTG ACAGCTGTGT ACTCTTAGGC TAAGAGATGT GACTACAGCC   1380
TGCCCCTGAC TGTGTTGTCC CAGGGCTGAT GCTGTACAGG TACAGGCTGG AGATTTTCAC   1440
ATAGGTTAGA TTCTCATTCA CGGGACTAGT TAGCTTTAAG CACCCTAGAG GACTAGGGTA   1500
ATCTGACTTC TCACTTCCTA AGTTCCCTTC TATATCCTCA AGGTAGAAAT GTCTATGTTT   1560
TCTACTCCAA TTCATAAATC TATTCATAAG TCTTTGGTAC AAGTTTACAT GATAAAAGA    1620
AATGTGATTT GTCTTCCCTT CTTTGCACTT TTGAAATAAA GTATTTATC              1669
```

(2) INFORMATION FOR SEQ ID NO:4:

(i) SEQUENCE CHARACTERISTICS:
        (A) LENGTH: 329 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Met Trp Gly Leu Lys Val Leu Leu Leu Pro Val Ser Phe Ala Leu
 1               5                  10                  15

Tyr Pro Glu Glu Ile Leu Asp Thr His Trp Glu Leu Trp Lys Lys Thr
            20                  25                  30

His Arg Lys Gln Tyr Asn Asn Lys Val Asp Glu Ile Ser Arg Arg Leu
```

```
              35                  40                  45
Ile Trp Glu Lys Asn Leu Lys Tyr Ile Ser Ile His Asn Leu Glu Ala
        50                  55                  60

Ser Leu Gly Val His Thr Tyr Glu Leu Ala Met Asn His Leu Gly Asp
 65                  70                  75                  80

Met Thr Ser Glu Glu Val Val Gln Lys Met Thr Gly Leu Lys Val Pro
                 85                  90                  95

Leu Ser His Ser Arg Ser Asn Asp Thr Leu Tyr Ile Pro Glu Trp Glu
                100                 105                 110

Gly Arg Ala Pro Asp Ser Val Asp Tyr Arg Lys Lys Gly Tyr Val Thr
            115                 120                 125

Pro Val Lys Asn Gln Gly Gln Cys Gly Ser Cys Trp Ala Phe Ser Ser
130                 135                 140

Val Gly Ala Leu Glu Gly Gln Leu Lys Lys Lys Thr Gly Lys Leu Leu
145                 150                 155                 160

Asn Leu Ser Pro Gln Asn Leu Val Asp Cys Val Ser Glu Asn Asp Gly
                165                 170                 175

Cys Gly Gly Gly Tyr Met Thr Asn Ala Phe Gln Tyr Val Gln Lys Asn
                180                 185                 190

Arg Gly Ile Asp Ser Glu Asp Ala Tyr Pro Tyr Val Gly Gln Glu Glu
            195                 200                 205

Ser Cys Met Tyr Asn Pro Thr Gly Lys Ala Ala Lys Cys Arg Gly Tyr
210                 215                 220

Arg Glu Ile Pro Glu Gly Asn Glu Lys Ala Leu Lys Arg Ala Val Ala
225                 230                 235                 240

Arg Val Gly Pro Val Ser Val Ala Ile Asp Ala Ser Leu Thr Ser Phe
                245                 250                 255

Gln Phe Tyr Ser Lys Gly Val Tyr Tyr Asp Glu Ser Cys Asn Ser Asp
                260                 265                 270

Asn Leu Asn His Ala Val Leu Ala Val Gly Tyr Gly Ile Gln Lys Gly
            275                 280                 285

Asn Lys His Trp Ile Ile Lys Asn Ser Trp Gly Glu Asn Trp Gly Asn
290                 295                 300

Lys Gly Tyr Ile Leu Met Ala Arg Asn Lys Asn Asn Ala Cys Gly Ile
305                 310                 315                 320

Ala Asn Leu Ala Ser Phe Pro Lys Met
                325

(2) INFORMATION FOR SEQ ID NO:5:

(i) SEQUENCE CHARACTERISTICS:
        (A) LENGTH: 1001 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:5:

CTGCAGGAAT TCGGCACGAG GGGTGCTATT GTGAGGCGGT TGTAGAAGTT AATAAAGGTA      60

TCCATGGAGA ACACTGAAAA CTCAGTGGAT TCAAAATCCA TTAAAAATTT GGAACCAAAG     120

ATCATACATG GAAGCGAATC AATGGACTCT GGAATATCCC TGGACAACAG TTATAAAATG     180

GATTATCCTG AGATGGGTTT ATGTATAATA ATTAATAATA AGAATTTTCA TAAGAGCACT     240

GGAATGACAT CTCGGTCTGG TACAGATGTC GATGCAGCAA ACCTCAGGGA AACATTCAGA     300
```

```
AACTTGAAAT ATGAAGTCAG GAATAAAAAT GATCTTACAC GTGAAGAAAT TGTGGAATTG    360

ATGCGTGATG TTTCTAAAGA AGATCACAGC AAAAGGAGCA GTTTTGTTTG TGTGCTTCTG    420

AGCCATGGTG AAGAAGGAAT AATTTTTGGA ACAAATGGAC CTGTTGACCT GAAAAAAATA    480

ACAAACTTTT TCAGAGGGGA TCGTTGTAGA AGTCTAACTG GAAAACCCAA ACTTTTCATT    540

ATTCAGGCCT GCCGTGGTAC AGAACTGGAC TGTGGCATTG AGACAGACAG TGGTGTTGAT    600

GATGACATGG CGTGTCATAA AATACCAGTG GAGGCCGACT TCTTGTATGC ATACTCCACA    660

GCACCTGGTT ATTATTCTTG GCGAAATTCA AAGGATGGCT CCTGGTTCAT CCAGTCGCTT    720

TGTGCCATGC TGAAACAGTA TGCCGACAAG CTTGAATTTA TGCACATTCT TACCCGGGTT    780

AACCGAAAGG TGGCAACAGA ATTTGAGTCC TTTTCCTTTG ACGCTACTTT TCATGCAAAG    840

AAACAGATTC CATGTATTGT TTCCATGCTC ACAAAAGAAC TCTATTTTTA TCACTAAAGA    900

AATGGTTGGT TGGTGGTTTT TTTTAGTTTG TATGCCAAGT GAGAAGATGG TATATTTGGT    960

ACTGTATTTC CCTCTCATTT TGACCTACTC TCATGCTGCA G                       1001
```

(2) INFORMATION FOR SEQ ID NO:6:

(i) SEQUENCE CHARACTERISTICS:
        (A) LENGTH: 277 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:6:

```
Met Glu Asn Thr Glu Asn Ser Val Asp Ser Lys Ser Ile Lys Asn Leu
 1               5                  10                  15

Glu Pro Lys Ile Ile His Gly Ser Glu Ser Met Asp Ser Gly Ile Ser
            20                  25                  30

Leu Asp Asn Ser Tyr Lys Met Asp Tyr Pro Glu Met Gly Leu Cys Ile
        35                  40                  45

Ile Ile Asn Asn Lys Asn Phe His Lys Ser Thr Gly Met Thr Ser Arg
    50                  55                  60

Ser Gly Thr Asp Val Asp Ala Ala Asn Leu Arg Glu Thr Phe Arg Asn
65                  70                  75                  80

Leu Lys Tyr Glu Val Arg Asn Lys Asn Asp Leu Thr Arg Glu Glu Ile
                85                  90                  95

Val Glu Leu Met Arg Asp Val Ser Lys Glu Asp His Ser Lys Arg Ser
            100                 105                 110

Ser Phe Val Cys Val Leu Leu Ser His Gly Glu Glu Gly Ile Ile Phe
        115                 120                 125

Gly Thr Asn Gly Pro Val Asp Leu Lys Lys Ile Thr Asn Phe Phe Arg
    130                 135                 140

Gly Asp Arg Cys Arg Ser Leu Thr Gly Lys Pro Lys Leu Phe Ile Ile
145                 150                 155                 160

Gln Ala Cys Arg Gly Thr Glu Leu Asp Cys Gly Ile Glu Thr Asp Ser
                165                 170                 175

Gly Val Asp Asp Asp Met Ala Cys His Lys Ile Pro Val Glu Ala Asp
            180                 185                 190

Phe Leu Tyr Ala Tyr Ser Thr Ala Pro Gly Tyr Tyr Ser Trp Arg Asn
        195                 200                 205

Ser Lys Asp Gly Ser Trp Phe Ile Gln Ser Leu Cys Ala Met Leu Lys
    210                 215                 220
```

Gln Tyr Ala Asp Lys Leu Glu Phe Met His Ile Leu Thr Arg Val Asn
225                 230                 235                 240

Arg Lys Val Ala Thr Glu Phe Glu Ser Phe Ser Phe Asp Ala Thr Phe
            245                 250                 255

His Ala Lys Lys Gln Ile Pro Cys Ile Val Ser Met Leu Thr Lys Glu
            260                 265                 270

Leu Tyr Phe Tyr His
        275

(2) INFORMATION FOR SEQ ID NO:7:

(i) SEQUENCE CHARACTERISTICS:
        (A) LENGTH: 963 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

ATGGAGATGG AAAAGGAGTT CGAGCAGATC GACAAGTCCG GGAGCTGGGC GGCCATTTAC        60

CAGGATATCC GACATGAAGC CAGTGACTTC CCATGTAGAG TGGCCAAGCT TCCTAAGAAC       120

AAAAACCGAA ATAGGTACAG AGACGTCAGT CCCTTTGACC ATAGTCGGAT TAAACTACAT       180

CAAGAAGATA ATGACTATAT CAACGCTAGT TTGATAAAAA TGGAAGAAGC CCAAAGGAGT       240

TACATTCTTA CCCAGGGCCC TTTGCCTAAC ACATGCGGTC ACTTTTGGGA GATGGTGTGG       300

GAGCAGAAAA GCAGGGGTGT CGTCATGCTC AACAGAGTGA TGGAGAAAGG TTCGTTAAAA       360

TGCGCACAAT ACTGGCCACA AAAGAAGAA AAAGAGATGA TCTTTGAAGA CACAAATTTG       420

AAATTAACAT TGATCTCTGA AGATATCAAG TCATATTATA CAGTGCGACA GCTAGAATTG       480

GAAAACCTTA CAACCCAAGA AACTCGAGAG ATCTTACATT TCCACTATAC CACATGGCCT       540

GACTTTGGAG TCCCTGAATC ACCAGCCTCA TTCTTGAACT TTCTTTTCAA AGTCCGAGAG       600

TCAGGGTCAC TCAGCCCGGA GCACGGGCCC GTTGTGGTGC ACAGCAGTGC AGGCATCGGC       660

AGGTCTGGAA CCTTCTGTCT GGCTGATACC TGCCTCCTGC TGATGGACAA GAGGAAAGAC       720

CCTTCTTCCG TTGATATCAA GAAAGTGCTG TTAGAAATGA GGAAGTTTCG GATGGGGTTG       780

ATCCAGACAG CCGACCAGCT GCGCTTCTCC TACCTGGCTG TGATCGAAGG TGCCAAATTC       840

ATCATGGGGG ACTCTTCCGT GCAGGATCAG TGGAAGGAGC TTTCCCACGA GGACCTGGAG       900

CCCCCACCCG AGCATATCCC CCCACCTCCC CGGCCACCCA AACGAATCCT GGAGCCACAC       960

TGA                                                                   963

(2) INFORMATION FOR SEQ ID NO:8:

(i) SEQUENCE CHARACTERISTICS:
        (A) LENGTH: 322 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:8:

Met Glu Met Glu Lys Glu Phe Glu Gln Ile Asp Lys Ser Gly Ser Trp
1               5                   10                  15

Ala Ala Ile Tyr Gln Asp Ile Arg His Glu Ala Ser Asp Phe Pro Cys
            20                  25                  30

Arg Val Ala Lys Leu Pro Lys Asn Lys Asn Arg Asn Arg Tyr Arg Asp

|         |         |         |         |         | 35      |         |         |         |         | 40      |         |         |         |         | 45      |         |
|---------|---------|---------|---------|---------|---------|---------|---------|---------|---------|---------|---------|---------|---------|---------|---------|---------|

Val Ser Pro Phe Asp His Ser Arg Ile Lys Leu His Gln Glu Asp Asn
 50                      55                      60

Asp Tyr Ile Asn Ala Ser Leu Ile Lys Met Glu Glu Ala Gln Arg Ser
 65                      70                      75                      80

Tyr Ile Leu Thr Gln Gly Pro Leu Pro Asn Thr Cys Gly His Phe Trp
                 85                      90                      95

Glu Met Val Trp Glu Gln Lys Ser Arg Gly Val Val Met Leu Asn Arg
             100                     105                     110

Val Met Glu Lys Gly Ser Leu Lys Cys Ala Gln Tyr Trp Pro Gln Lys
         115                     120                     125

Glu Glu Lys Glu Met Ile Phe Glu Asp Thr Asn Leu Lys Leu Thr Leu
130                     135                     140

Ile Ser Glu Asp Ile Lys Ser Tyr Tyr Thr Val Arg Gln Leu Glu Leu
145                     150                     155                     160

Glu Asn Leu Thr Thr Gln Glu Thr Arg Glu Ile Leu His Phe His Tyr
                 165                     170                     175

Thr Thr Trp Pro Asp Phe Gly Val Pro Glu Ser Pro Ala Ser Phe Leu
             180                     185                     190

Asn Phe Leu Phe Lys Val Arg Glu Ser Gly Ser Leu Ser Pro Glu His
         195                     200                     205

Gly Pro Val Val His Ser Ser Ala Gly Ile Gly Thr Cys Gly Arg
210                     215                     220

Ser Gly Thr Phe Cys Leu Ala Asp Thr Cys Leu Leu Met Asp Lys
225                     230                     235                     240

Arg Lys Asp Pro Ser Ser Val Asp Ile Lys Lys Val Leu Leu Glu Met
                 245                     250                     255

Arg Lys Phe Arg Met Gly Leu Ile Gln Thr Ala Asp Gln Leu Arg Phe
             260                     265                     270

Ser Tyr Leu Ala Val Ile Glu Gly Ala Lys Phe Ile Met Gly Asp Ser
         275                     280                     285

Ser Val Gln Asp Gln Trp Lys Glu Leu Ser His Glu Asp Leu Glu Pro
290                     295                     300

Pro Pro Glu His Ile Pro Pro Pro Arg Pro Lys Arg Ile Leu
305                     310                     315                     320

Glu Pro (2) INFORMATION FOR SEQ ID NO:9:

(i) SEQUENCE CHARACTERISTICS:
        (A) LENGTH: 1001 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

```
CTGCAGGAAT TCGGCACGAG GGGTGCTATT GTGAGGCGGT TGTAGAAGTT AATAAAGGTA      60

TCCATGGAGA ACACTGAAAA CTCAGTGGAT TCAAAATCCA TTAAAAATTT GGAACCAAAG     120

ATCATACATG GAAGCGAATC AATGGACTCT GGAATATCCC TGGACAACAG TTATAAAATG     180

GATTATCCTG AGATGGGTTT ATGTATAATA ATTAATAATA AGAATTTTCA TAAGAGCACT     240

GGAATGACAT CTCGGTCTGG TACAGATGTC GATGCAGCAA ACCTCAGGGA ACATTCAGA      300

AACTTGAAAT ATGAAGTCAG GAATAAAAAT GATCTTACAC GTGAAGAAAT TGTGGAATTG     360
```

-continued

```
ATGCGTGATG TTTCTAAAGA AGATCACAGC AAAAGGAGCA GTTTTGTTTG TGTGCTTCTG      420

AGCCATGGTG AAGAAGGAAT AATTTTTGGA ACAAATGGAC CTGTTGACCT GAAAAAAATA      480

ACAAACTTTT TCAGAGGGGA TCGTTGTAGA AGTCTAACTG GAAAACCCAA ACTTTTCATT      540

ATTCAGGCCT CCCGTGGTAC AGAACTGGAC TGTGGCATTG AGACAGACAG TGGTGTTGAT      600

GATGACATGG CGTGTCATAA AATACCAGTG GAGGCCGACT TCTTGTATGC ATACTCCACA      660

GCACCTGGTT ATTATTCTTG GCGAAATTCA AAGGATGGCT CCTGGTTCAT CCAGTCGCTT      720

TGTGCCATGC TGAAACAGTA TGCCGACAAG CTTGAATTTA TGCACATTCT TACCCGGGTT      780

AACCGAAAGG TGGCAACAGA ATTTGAGTCC TTTTCCTTTG ACGCTACTTT TCATGCAAAG      840

AAACAGATTC CATGTATTGT TTCCATGCTC ACAAAAGAAC TCTATTTTTA TCACTAAAGA      900

AATGGTTGGT TGGTGGTTTT TTTTAGTTTG TATGCCAAGT GAGAAGATGG TATATTTGGT      960

ACTGTATTTC CCTCTCATTT TGACCTACTC TCATGCTGCA G                         1001
```

(2) INFORMATION FOR SEQ ID NO:10:

(i) SEQUENCE CHARACTERISTICS:
        (A) LENGTH: 277 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:10:

```
Met Glu Asn Thr Glu Asn Ser Val Asp Ser Lys Ser Ile Lys Asn Leu
 1               5                  10                  15

Glu Pro Lys Ile Ile His Gly Ser Glu Ser Met Asp Ser Gly Ile Ser
            20                  25                  30

Leu Asp Asn Ser Tyr Lys Met Asp Tyr Pro Glu Met Gly Leu Cys Ile
        35                  40                  45

Ile Ile Asn Asn Lys Asn Phe His Lys Ser Thr Gly Met Thr Ser Arg
    50                  55                  60

Ser Gly Thr Asp Val Asp Ala Ala Asn Leu Arg Glu Thr Phe Arg Asn
65                  70                  75                  80

Leu Lys Tyr Glu Val Arg Asn Lys Asn Asp Leu Thr Arg Glu Glu Ile
                85                  90                  95

Val Glu Leu Met Arg Asp Val Ser Lys Glu Asp His Ser Lys Arg Ser
            100                 105                 110

Ser Phe Val Cys Val Leu Leu Ser His Gly Glu Glu Gly Ile Ile Phe
        115                 120                 125

Gly Thr Asn Gly Pro Val Asp Leu Lys Lys Ile Thr Asn Phe Phe Arg
    130                 135                 140

Gly Asp Arg Cys Arg Ser Leu Thr Gly Lys Pro Lys Leu Phe Ile Ile
145                 150                 155                 160

Gln Ala Ser Arg Gly Thr Glu Leu Asp Cys Gly Ile Glu Thr Asp Ser
                165                 170                 175

Gly Val Asp Asp Asp Met Ala Cys His Lys Ile Pro Val Glu Ala Asp
            180                 185                 190

Phe Leu Tyr Ala Tyr Ser Thr Ala Pro Gly Tyr Tyr Ser Trp Arg Asn
        195                 200                 205

Ser Lys Asp Gly Ser Trp Phe Ile Gln Ser Leu Cys Ala Met Leu Lys
    210                 215                 220

Gln Tyr Ala Asp Lys Leu Glu Phe Met His Ile Leu Thr Arg Val Asn
```

```
                225                 230                 235                 240
Arg Lys Val Ala Thr Glu Phe Glu Ser Phe Ser Asp Ala Thr Phe
                    245                 250                 255
His Ala Lys Lys Gln Ile Pro Cys Ile Val Ser Met Leu Thr Lys Glu
                260                 265                 270
Leu Tyr Phe Tyr His
        275

(2) INFORMATION FOR SEQ ID NO:11:

(i) SEQUENCE CHARACTERISTICS:
        (A) LENGTH: 148 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:11:

Met Ser Gly Ile Ser Leu Asp Asn Ser Tyr Lys Met Asp Tyr Pro Glu
1               5                   10                  15
Met Gly Leu Cys Ile Ile Asn Asn Lys Asn Phe His Lys Ser Thr
            20                  25                  30
Gly Met Thr Ser Arg Ser Gly Thr Asp Val Asp Ala Ala Asn Leu Arg
        35                  40                  45
Glu Thr Phe Arg Asn Leu Lys Tyr Glu Val Arg Asn Lys Asn Asp Leu
50                  55                  60
Thr Arg Glu Glu Ile Val Glu Leu Met Arg Asp Val Ser Lys Glu Asp
65                  70                  75                  80
His Ser Lys Arg Ser Ser Phe Val Cys Val Leu Leu Ser His Gly Glu
                85                  90                  95
Glu Gly Ile Ile Phe Gly Thr Asn Gly Pro Val Asp Leu Lys Lys Ile
            100                 105                 110
Thr Asn Phe Phe Arg Gly Asp Arg Cys Arg Ser Leu Thr Gly Lys Pro
        115                 120                 125
Lys Leu Phe Ile Ile Gln Ala Ser Arg Gly Thr Glu Leu Asp Cys Gly
    130                 135                 140
Ile Glu Thr Asp
145

(2) INFORMATION FOR SEQ ID NO:12:

(i) SEQUENCE CHARACTERISTICS:
        (A) LENGTH: 990 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

ATGTGGGGGC TCAAGGTTCT GCTGCTACCT GTGGTGAGCT TGCTCTGTA CCCTGAGGAG      60

ATACTGGACA CCCACTGGGA GCTATGGAAG AAGACCCACA GGAAGCAATA TAACAACAAG    120

GTGGATGAAA TCTCTCGGCG TTTAATTTGG GAAAAAAACC TGAAGTATAT TTCCATCCAT    180

AACCTTGAGG CTTCTCTTGG TGTCCATACA TATGAACTGG CTATGAACCA CCTGGGGGAC    240

ATGACCAGTG AAGAGGTGGT TCAGAAGATG ACTGGACTCA AAGTACCCCT GTCTCATTCC    300

CGCAGTAATG ACACCCTTTA TCCCAGAA TGGGAAGGTA GAGCCCCAGA CTCTGTCGAC      360
```

-continued

| | |
|---|---|
| TATCGAAAGA AAGGATATGT TACTCCTGTC AAAAATCAGG GTCAGTGTGG TTCCTCTTGG | 420 |
| GCTTTTAGCT CTGTGGGTGC CCTGGAGGGC CAACTCAAGA AGAAAACTGG CAAACTCTTA | 480 |
| AATCTGAGTC CCCAGAACCT AGTGGATTGT GTGTCTGAGA ATGATGGCTG TGGAGGGGGC | 540 |
| TACATGACCA ATGCCTTCCA ATATGTGCAG AAGAACCGGG GTATTGACTC TGAAGATGCC | 600 |
| TACCCATATG TGGGACAGGA AGAGAGTTGT ATGTACAACC CAACAGGCAA GGCAGCTAAA | 660 |
| TGCAGAGGGT ACAGAGAGAT CCCCGAGGGG AATGAGAAAG CCCTGAAGAG GGCAGTGGCC | 720 |
| CGAGTGGGAC CTGTCTCTGT GGCCATTGAT GCAAGCCTGA CCTCCTTCCA GTTTTACAGC | 780 |
| AAAGGTGTGT ATTATGATGA AAGCTGCAAT AGCGATAATC TGAACCATGC GGTTTTGGCA | 840 |
| GTGGGATATG GAATCCAGAA GGGAAACAAG CACTGGATAA TTAAAAACAG CTGGGGAGAA | 900 |
| AACTGGGGAA ACAAAGGATA TATCCTCATG GCTCGAAATA AGAACAACGC CTGTGGCATT | 960 |
| GCCAACCTGG CCAGCTTCCC CAAGATGTGA | 990 |

(2) INFORMATION FOR SEQ ID NO:13:

(i) SEQUENCE CHARACTERISTICS:
        (A) LENGTH: 990 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

| | |
|---|---|
| ATGTGGGGC TCAAGGTTCT GCTGCTACCT GTGGTGAGCT TTGCTCTGTA CCCTGAGGAG | 60 |
| ATACTGGACA CCCACTGGGA GCTATGGAAG AAGACCCACA GGAAGCAATA TAACAACAAG | 120 |
| GTGGATGAAA TCTCTCGGCG TTTAATTTGG GAAAAAAACC TGAAGTATAT TTCCATCCAT | 180 |
| AACCTTGAGG CTTCTCTTGG TGTCCATACA TATGAACTGG CTATGAACCA CCTGGGGGAC | 240 |
| ATGACCAGTG AAGAGGTGGT TCAGAAGATG ACTGGACTCA AAGTACCCCT GTCTCATTCC | 300 |
| CGCAGTAATG ACACCCTTTA TATCCCAGAA TGGGAAGGTA GAGCCCCAGA CTCTGTCGAC | 360 |
| TATCGAAAGA AAGGATATGT TACTCCTGTC AAAAATCAGG GTCAGTGTGG TTCCGCTTGG | 420 |
| GCTTTTAGCT CTGTGGGTGC CCTGGAGGGC CAACTCAAGA AGAAAACTGG CAAACTCTTA | 480 |
| AATCTGAGTC CCCAGAACCT AGTGGATTGT GTGTCTGAGA ATGATGGCTG TGGAGGGGGC | 540 |
| TACATGACCA ATGCCTTCCA ATATGTGCAG AAGAACCGGG GTATTGACTC TGAAGATGCC | 600 |
| TACCCATATG TGGGACAGGA AGAGAGTTGT ATGTACAACC CAACAGGCAA GGCAGCTAAA | 660 |
| TGCAGAGGGT ACAGAGAGAT CCCCGAGGGG AATGAGAAAG CCCTGAAGAG GGCAGTGGCC | 720 |
| CGAGTGGGAC CTGTCTCTGT GGCCATTGAT GCAAGCCTGA CCTCCTTCCA GTTTTACAGC | 780 |
| AAAGGTGTGT ATTATGATGA AAGCTGCAAT AGCGATAATC TGAACCATGC GGTTTTGGCA | 840 |
| GTGGGATATG GAATCCAGAA GGGAAACAAG CACTGGATAA TTAAAAACAG CTGGGGAGAA | 900 |
| AACTGGGGAA ACAAAGGATA TATCCTCATG GCTCGAAATA AGAACAACGC CTGTGGCATT | 960 |
| GCCAACCTGG CCAGCTTCCC CAAGATGTGA | 990 |

(2) INFORMATION FOR SEQ ID NO:14:

(i) SEQUENCE CHARACTERISTICS:
        (A) LENGTH: 329 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

```
Met Trp Gly Leu Lys Val Leu Leu Pro Val Val Ser Phe Ala Leu
 1               5                  10                  15

Tyr Pro Glu Glu Ile Leu Asp Thr His Trp Glu Leu Trp Lys Lys Thr
                20                  25                  30

His Arg Lys Gln Tyr Asn Asn Lys Val Asp Glu Ile Ser Arg Arg Leu
                35                  40                  45

Ile Trp Glu Lys Asn Leu Lys Tyr Ile Ser Ile His Asn Leu Glu Ala
 50                  55                  60

Ser Leu Gly Val His Thr Tyr Glu Leu Ala Met Asn His Leu Gly Asp
 65                  70                  75                  80

Met Thr Ser Glu Glu Val Val Gln Lys Met Thr Gly Leu Lys Val Pro
                85                  90                  95

Leu Ser His Ser Arg Ser Asn Asp Thr Leu Tyr Ile Pro Glu Trp Glu
                100                 105                 110

Gly Arg Ala Pro Asp Ser Val Asp Tyr Arg Lys Lys Gly Tyr Val Thr
                115                 120                 125

Pro Val Lys Asn Gln Gly Gln Cys Gly Ser Ser Trp Ala Phe Ser Ser
130                 135                 140

Val Gly Ala Leu Glu Gly Gln Leu Lys Lys Thr Gly Lys Leu Leu
145                 150                 155                 160

Asn Leu Ser Pro Gln Asn Leu Val Asp Cys Val Ser Glu Asn Asp Gly
                165                 170                 175

Cys Gly Gly Gly Tyr Met Thr Asn Ala Phe Gln Tyr Val Gln Lys Asn
                180                 185                 190

Arg Gly Ile Asp Ser Glu Asp Ala Tyr Pro Tyr Val Gly Gln Glu Glu
                195                 200                 205

Ser Cys Met Tyr Asn Pro Thr Gly Lys Ala Ala Lys Cys Arg Gly Tyr
210                 215                 220

Arg Glu Ile Pro Glu Gly Asn Glu Lys Ala Leu Lys Arg Ala Val Ala
225                 230                 235                 240

Arg Val Gly Pro Val Ser Val Ala Ile Asp Ala Ser Leu Thr Ser Phe
                245                 250                 255

Gln Phe Tyr Ser Lys Gly Val Tyr Tyr Asp Glu Ser Cys Asn Ser Asp
                260                 265                 270

Asn Leu Asn His Ala Val Leu Ala Val Gly Tyr Gly Ile Gln Lys Gly
                275                 280                 285

Asn Lys His Trp Ile Ile Lys Asn Ser Trp Gly Glu Asn Trp Gly Asn
290                 295                 300

Lys Gly Tyr Ile Leu Met Ala Arg Asn Lys Asn Asn Ala Cys Gly Ile
305                 310                 315                 320

Ala Asn Leu Ala Ser Phe Pro Lys Met
                325
```

(2) INFORMATION FOR SEQ ID NO:15:

(i) SEQUENCE CHARACTERISTICS:
        (A) LENGTH: 329 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:15:

-continued

```
Met Trp Gly Leu Lys Val Leu Leu Pro Val Val Ser Phe Ala Leu
 1               5                  10                  15

Tyr Pro Glu Glu Ile Leu Asp Thr His Trp Glu Leu Trp Lys Lys Thr
            20                  25                  30

His Arg Lys Gln Tyr Asn Asn Lys Val Asp Glu Ile Ser Arg Arg Leu
        35                  40                  45

Ile Trp Glu Lys Asn Leu Lys Tyr Ile Ser Ile His Asn Leu Glu Ala
 50                  55                  60

Ser Leu Gly Val His Thr Tyr Glu Leu Ala Met Asn His Leu Gly Asp
 65                  70                  75                  80

Met Thr Ser Glu Glu Val Val Gln Lys Met Thr Gly Leu Lys Val Pro
            85                  90                  95

Leu Ser His Ser Arg Ser Asn Asp Thr Leu Tyr Ile Pro Glu Trp Glu
            100                 105                 110

Gly Arg Ala Pro Asp Ser Val Asp Tyr Arg Lys Lys Gly Tyr Val Thr
            115                 120                 125

Pro Val Lys Asn Gln Gly Gln Cys Gly Ser Ala Trp Ala Phe Ser Ser
 130                 135                 140

Val Gly Ala Leu Glu Gly Gln Leu Lys Lys Lys Thr Gly Lys Leu Leu
145                 150                 155                 160

Asn Leu Ser Pro Gln Asn Leu Val Asp Cys Val Ser Glu Asn Asp Gly
                165                 170                 175

Cys Gly Gly Gly Tyr Met Thr Asn Ala Phe Gln Tyr Val Gln Lys Asn
                180                 185                 190

Arg Gly Ile Asp Ser Glu Asp Ala Tyr Pro Tyr Val Gly Gln Glu Glu
                195                 200                 205

Ser Cys Met Tyr Asn Pro Thr Gly Lys Ala Ala Lys Cys Arg Gly Tyr
    210                 215                 220

Arg Glu Ile Pro Glu Gly Asn Glu Lys Ala Leu Lys Arg Ala Val Ala
225                 230                 235                 240

Arg Val Gly Pro Val Ser Val Ala Ile Asp Ala Ser Leu Thr Ser Phe
                245                 250                 255

Gln Phe Tyr Ser Lys Gly Val Tyr Tyr Asp Glu Ser Cys Asn Ser Asp
                260                 265                 270

Asn Leu Asn His Ala Val Leu Ala Val Gly Tyr Gly Ile Gln Lys Gly
                275                 280                 285

Asn Lys His Trp Ile Ile Lys Asn Ser Trp Gly Glu Asn Trp Gly Asn
    290                 295                 300

Lys Gly Tyr Ile Leu Met Ala Arg Asn Lys Asn Asn Ala Cys Gly Ile
305                 310                 315                 320

Ala Asn Leu Ala Ser Phe Pro Lys Met
                325
```